US012661320B2

(12) United States Patent
Sosnik et al.

(10) Patent No.: US 12,661,320 B2
(45) Date of Patent: Jun. 23, 2026

(54) HYBRID POLYMER-CERAMIC PARTICLES, METHODS FOR PREPARING THE SAME AND USES THEREOF

(71) Applicant: TECHNION RESEARCH & DEVELOPMENT FOUNDATION LIMITED, Haifa (IL)

(72) Inventors: Alejandro Dario Sosnik, Haifa (IL); Vladislav Kushnirov Melnitzer, Nesher (IL)

(73) Assignee: TECHNION RESEARCH & DEVELOPMENT FOUNDATION LIMITED, Haifa (CN)

( * ) Notice: Subject to any disclaimer, the term of this patent is extended or adjusted under 35 U.S.C. 154(b) by 714 days.

(21) Appl. No.: 17/268,484

(22) PCT Filed: Aug. 13, 2019

(86) PCT No.: PCT/IL2019/050907

§ 371 (c)(1),
(2) Date: Feb. 15, 2021

(87) PCT Pub. No.: WO2020/035858

PCT Pub. Date: Feb. 20, 2020

(65) Prior Publication Data

US 2021/0177759 A1 Jun. 17, 2021

Related U.S. Application Data

(60) Provisional application No. 62/718,014, filed on Aug. 13, 2018.

(51) Int. Cl.

*A61K 9/16* (2006.01)
*A61K 9/00* (2006.01)
*A61K 41/00* (2020.01)
*A61K 47/02* (2006.01)
*A61K 47/34* (2017.01)

(52) U.S. Cl.

CPC .......... *A61K 9/1635* (2013.01); *A61K 9/0009* (2013.01); *A61K 9/1647* (2013.01); *A61K 41/0033* (2013.01); *A61K 47/02* (2013.01); *A61K 47/34* (2013.01)

(58) Field of Classification Search

None
See application file for complete search history.

(56) References Cited

U.S. PATENT DOCUMENTS

2004/0022861 A1 * 2/2004 Williams, III ....... A61K 9/1647 514/7.7

FOREIGN PATENT DOCUMENTS

WO WO-2006026840 A2 * 3/2006 ........... A61K 9/1611
WO WO-2018144954 A1 * 8/2018 ............ A61K 47/24

OTHER PUBLICATIONS

Hu et al. (Drug-Loaded and Superparamagnetic Iron Oxide Nanoparticle Surface-Embedded Amphiphilic Block Copolymer Micelles for Integrated Chemotherapeutic Drug Delivery and MR Imaging, Langmuir, 2012). (Year: 2012).*

Mdlovu et al. (Iron oxide-pluronic F127 polymer nanocomposites as carriers for a doxorubicin drug delivery system, Colloids and Surfaces A, 2019) and Tiet et al. (WO 2018/144954 A1) (Year: 2019).*

Li et al. (Green Synthetic, Multifunctional Hybrid Micelles with Shell Embedded Magnetic Nanoparticles for Theranostic Applications, ACS Appl. Mater. Interfaces, 2013) (Year: 2013).*

Fattakhova-Rohlfing et al., Three-Dimensional Titanium Dioxide Nanomaterials, Chemical Reviews, 2014 (Year: 2014).*

Glaubitz et al., Designing the ultrasonic treatment of nanoparticle-dispersions via machine learning, Nanoscale, 2022 (Year: 2022).*

Lai et al. (Multifunctional doxorubicin/superparamagnetic iron oxide-encapsulated Pluronic F127 micelles used for chemotherapy/magnetic resonance imaging, Journal of Applied Physics, 2010) (Year: 2010).*

Yu et al. (Polymeric Drug Delivery System Based on Pluronics for Cancer Treatment, Molecules, 2021) (Year: 2021).*

Clayton et al. (Physical characterization of nanoparticle size and surface modification using particle scattering diffusometry, Biomicrofluidics, 2016) (Year: 2016).*

Bogdan (Nanoparticles of Titanium and Zinc Oxides as Novel Agents in Tumor Treatment: A Review, Nanoscale Research Letters, 2017) (Year: 2017).* https://particularmaterials.com/index.php/nanoparticles-characteristics/monodispersity/ (Year: 2018).*

Plisko et al (Effect of Pluronic F127 on porous and dense membrane structure formation via non-solvent induced and evaporation induced phase separation, Journal of Membrane Science, 2019) (Year: 2019).*

Hu J, Qian Y, Wang X, Liu T, Liu S. Drug-loaded and superparamagnetic iron oxide nanoparticle surface-embedded amphiphilic block copolymer micelles for integrated chemotherapeutic drug delivery and MR imaging. Langmuir. Jan. 31, 2012;28(4):2073-82. doi: 10.1021/la203992q. Epub Nov. 11, 2011. PMID: 22047551.

Huo Q, Liu J, Wang LQ, Jiang Y, Lambert TN, Fang E. A new class of silica cross-linked micellar core-shell nanoparticles. J Am Chem Soc. May 17, 2006;128(19):6447-53. doi: 10.1021/ja060367p. PMID: 16683810.

(Continued)

*Primary Examiner* — Andrew S Rosenthal
*Assistant Examiner* — Danielle Kim
(74) *Attorney, Agent, or Firm* — The Roy Gross Law Firm, LLC; Roy D. Gross

(57) ABSTRACT

Particles comprised of a transition metal oxide and an amphiphilic copolymer, having a predetermined particle size, and uses same for encapsulation of hydrophobic compounds and for sono-responsive therapy, are disclosed. The methods of manufacturing the particles with a predetermined particle size are disclosed.

19 Claims, 15 Drawing Sheets

(56) References Cited

OTHER PUBLICATIONS

Kushnirov Melnitzer, V., & Sosnik, A. (2018). Hybrid Titanium Oxide/Polymer Amphiphilic Nanomaterials with Controlled Size for Drug Encapsulation and Delivery. Advanced Functional Materials, 1806146. doi:10.1002/adfm.201806146.
Li Y, Ma J, Zhu H, Gao X, Dong H, Shi D. Green synthetic, multifunctional hybrid micelles with shell embedded magnetic nanoparticles for theranostic applications. ACS Appl Mater Interfaces. Aug. 14, 2013;5(15):7227-35. doi: 10.1021/am401573b. Epub Jul. 12, 2013. PMID: 23815498.
Sosnik A, Cohn D. Ethoxysilane-capped PEO-PPO-PEO triblocks: a new family of reverse thermo-responsive polymers. Biomaterials. Jun. 2004;25(14):2851-8. doi: 10.1016/j.biomaterials.2003.09.057. PMID: 14962563.
Steunou, N., Ribot, F., Boubekeur, K., Maquet, J., & Sanchez, C. (1999). Ketones as an oxolation source for the synthesis of titanium-oxo-organoclusters. New Journal of Chemistry, 23(11), 1079-1086. doi:10.1039/a904760c.
You, D. G., Deepagan, V. G., Um, W., Jeon, S., Son, S., Chang, H., & Park, J. H. (2016). ROS-generating TiO 2 nanoparticles for non-invasive sonodynamic therapy of cancer. Scientific reports, 6(1), 1-12.
Sanchez, C., Soler-Illia, G. J. de A. A., Ribot, F., Lalot, T., Mayer, C. R., & Cabuil, V. (2001). Designed Hybrid Organic—Inorganic Nanocomposites from Functional Nanobuilding Blocks. Chemistry of Materials, 13(10), 3061-3083. doi:10.1021/cm011061e.
Sasidharan, M., Zenibana, H., Nandi, M., Bhaumik, A., & Nakashima, K. (2013). Synthesis of mesoporous hollow silica nanospheres using polymeric micelles as template and their application as a drug-delivery carrier. Dalton Transactions, 42(37), 13381. doi:10.1039/c3dt51267c.
Khanal A, Inoue Y, Yada M, Nakashima K. Synthesis of silica hollow nanoparticles templated by polymeric micelle with core-shell-corona structure. J Am Chem Soc. Feb. 14, 2007;129(6):1534-5. doi: 10.1021/ja0684904. PMID: 17283999.
Sasidharan, M., & Nakashima, K. Core-Shell-Corona Polymeric Micelles as a Versatile Template for Synthesis of Inorganic Hollow Nanospheres. Acc. Chem. Res. 2014, 47, 1, 157-167. doi:10.1021/ar4001026.
Y. Liu, J. Goebla, Y. Yin. Templated synthesis of nanostructured materials. Chem. Soc. Rev., 2013,42, 2610-2653.
Hüsing, N., Schubert, U. Porous Inorganic-Organic Hybrid Materials. In P. Gómez-Romero & C. Sanchez (Eds.), Functional Hybrid Materials (pp. 86-121). Wiley-VCH Verlag GmbH Co. KGaA. (2004).
Talal, J., Abutbul-Ionita, I., Schlachet, I., Danino, D., & Sosnik, A. (2017). Amphiphilic Nanoparticle-in-Nanoparticle Drug Delivery Systems Exhibiting Cross-Linked Inorganic Rate-Controlling Domains. Chemistry of Materials, 29(2), 873-885. doi:10.1021/acs.chemmater.6b04922.
J. L. Vivero-Escoto, Y.-D. Chiang, K. Wu, Y. Yamauchi, Recent progress in mesoporous titania materials: adjusting morphology for innovative applications. Sci. Technol. Adv. Mater. 2012, 13, 013003.
Cargnello, M., Gordon, T. R., & Murray, C. B. (2014). Solution-phase synthesis of titanium dioxide nanoparticles and nanocrystals. Chemical reviews, 114(19), 9319-9345.
Rozes, L., & Sanchez, C. (2011). Titanium oxo-clusters: precursors for a Lego-like construction of nanostructured hybrid materials. Chemical Society Reviews, 40(2), 1006-1030.
C. Sanchez, L. Rozes, F. Ribot, C. Laberty-Robert, D. Grosso, C. Sassoye, C. Boissiere, L. Nicole, Chimie douce: A and of opportunities for the designed construction of functional inorganic and hybrid organic-inorganic nanomaterials. C. R. Chim. 2010, 13, 3.
S. Trabelsi, A. Janke, R. Hassler, N. E. Zaferopoulos, G. Fornasieri, S. Bocchini, L. Rozes, M. Stamm, J.-F. Gérard, C. Sanchez, Novel Organo-Functional Titanium-oxo-cluster-Based Hybrid Materials with Enhanced Thermomechanical and Thermal Properties. Macromolecules 2005, 38, 6068.
Jie Hou, Junyi Hu, Qing Sun, Guanyun Zhang, Chen-Ho Tung, and Yifeng Wang. A Post-Functionalizable Iso-Polyoxotitanate Cage Cluster. Inorganic Chemistry 2016 55 (14), 7075-7078 DOI: 10.1021/acs.inorgchem.6b00982.
Chiappetta, D. A., Alvarez-Lorenzo, C., Rey-Rico, A., Taboada, P., Concheiro, A., & Sosnik, A. (2010). N-alkylation of poloxamines modulates micellar assembly and encapsulation and release of the antiretroviral efavirenz. European Journal of Pharmaceutics and Biopharmaceutics, 76(1), 24-37. doi:10.1016/j.ejpb.2010.05.007.
Chiappetta DA, Hocht C, Taira C, Sosnik A. Oral pharmacokinetics of the anti-HIV efavirenz encapsulated within polymeric micelles. Biomaterials. Mar. 2011;32(9):2379-87. doi: 10.1016/j.biomaterials.2010.11.082. Epub Dec. 24, 2010. PMID: 21186055.
Glisoni, R. J., & Sosnik, A. (2014). Encapsulation of the antimicrobial and immunomodulator agent nitazoxanide within polymeric micelles. Journal of nanoscience and nanotechnology, 14(6), 4670-4682.
Moretton, M. A., Chiappetta, D. A., & Sosnik, A. (2012). Cryoprotection-lyophilization and physical stabilization of rifampicin-loaded flower-like polymeric micelles. Journal of The Royal Society Interface, 9(68), 487-502.
Mousavi, S. D., Maghsoodi, F., Panahandeh, F., Yazdian-Robati, R., Reisi-Vanani, A., & Tafaghodi, M. (2018). Doxorubicin delivery via magnetic nanomicelles comprising from reduction-responsive poly (ethylene glycol)-b-poly (εcaprolactone)(PEG-SS-PCL) and loaded with superparamagnetic iron oxide (SPIO) nanoparticles: Preparation, characterization and simulation. Materials Science and Engineering: C, 92, 631-643.
PCT International Search Report for International Application No. PCT/IL2019/050907, mailed Dec. 9, 2019, 3pp.
PCT Written Opinion for International Application No. PCT/IL2019/050907, mailed Dec. 9, 2019, 11pp.

* cited by examiner

HYBRID POLYMER-CERAMIC PARTICLES, METHODS FOR PREPARING THE SAME AND USES THEREOF

CROSS REFERENCE TO RELATED APPLICATIONS

This application is a National Phase of PCT Patent Application No. PCT/IL2019/050907 having International filing date of Aug. 13, 2019, which claims the benefit of priority to U.S. Provisional Patent Application No. 62/718,014 filed Aug. 13, 2018, entitled "HYBRID POLYMER-CERAMIC PARTICLES FOR DRUG ENCAPSULATION AND DELIVERY, METHODS FOR PREPARING THE SAME AND USES THEREOF" the contents of which are incorporated herein by reference in their entirety.

FIELD OF THE INVENTION

This invention is inter alia directed to hybrid particles comprising an amphiphilic copolymer and a transition metal-oxide and uses thereof, such as for encapsulating and releasing therapeutically active agents and for sonodynamic therapy.

BACKGROUND OF THE INVENTION

Amphiphilic polymeric nanoparticles are among the most clinically relevant drug nano-carriers produced by the self-assembly of amphiphilic block or graft copolymers. Their physical stability is usually jeopardized under extreme dilution in the biological medium. Moreover, their ability to control the release of the encapsulated drug is low. The design and synthesis of polymer-ceramic hybrid nanomaterials aims to capitalize on the features of each component. The incorporation of a ceramic shield confers physical and mechanical stability and by controlling its porosity, the release kinetics can be fine-tuned. In addition, some ceramic biomaterials can be used to promote hydroxyapatite deposition and bone growth.

However, synthesizing titanium oxide (titania) nano-particles by convenient sol-gel techniques is quite challenging, since titanium alkoxide precursors are extremely moisture sensitive and hydrolyze spontaneously upon contact with water, resulting in formation of particles with unpredictable size and morphology. Several attempts were performed to synthesize titania nano-particles having a controllable particle size, however, they used expensive methodologies (e.g. atomic layer deposition) which are not feasible for the industrial mass production.

SUMMARY OF THE INVENTION

In one aspect of the invention, provided herein is a particle comprising:

(i) an amphiphilic copolymer comprising a first block forming a hydrophobic core, and a second block having a water solubility greater than the first block and (ii) a transition metal oxide;

wherein the transition metal oxide is bound to the second block, thereby forming a hydrophilic shell.

In one embodiment, the particle further comprises a hydrophobic compound bound to the hydrophobic core.

In one embodiment, the amphiphilic copolymer is characterized by self-assembly in an aqueous solution.

In one embodiment, the self-assembly comprises forming a micelle-like structure.

In one embodiment, the amphiphilic copolymer is characterized by a hydrophilic-lipophilic balance (HLB) value that ranges from 1 to 24.

In one embodiment, the second block comprises a substantially water soluble polymer selected from the group consisting of a water-soluble polyether, a polysaccharide, a polyester, a polyphosphoester, a polyanhydride, a polyamide, a polyacrylamide, a polyacrylate, a polymetacrylate, a polyvinyl alcohol, a poly(oxazoline), a polypeptide or any combination thereof.

In one embodiment, the first block comprises a substantially water insoluble compound selected from the group consisting of: a polyether, a polylactic acid, a polylactate ester, a polyglycolic acid, a polyglycolate ester, a polystyrene, a polycaprolactone, a phospholipid, and a fatty acid, or any combination thereof.

In one embodiment, a weight per weight (w/w) ratio of the first block to the second block within the amphiphilic copolymer is in a range from 1 to 99%.

In one embodiment, a w/w ratio of the metal oxide to the amphiphilic copolymer ranges from 10 to 90% of the nanoparticle.

In one embodiment, the particle retains its structural and chemical identity in a physiological environment for at least 2 h.

In one embodiment, the hydrophobic compound is substantially released from the particle.

In one embodiment, a w/w concentration of the hydrophobic compound within the particle ranges from 1 to 50%.

In one embodiment, the hydrophobic compound substantially retains its activity within the particle.

In one embodiment, the hydrophobic compound is selected from the group consisting of: a pharmaceutically active agent, a labeling agent, a diagnostic agent, a prophylactic agent, a surface-modifying agent, a nutraceutical, or any combination thereof.

In one embodiment, the hydrophobic compound is water-insoluble.

In one embodiment, the particle is characterized by a predetermined size.

In another aspect of the invention, provided herein is a composition, comprising a plurality of particles of the invention.

In one embodiment, the plurality of particles is characterized by a predetermined particle size in a range from 1 to 500 nm.

In one embodiment, the plurality of particles is characterized by a polydispersity index being in a range from 0.01 to 0.5.

In one embodiment, the amphiphilic copolymer is substantially biodegradable in a physiological environment.

In another aspect of the invention, provided herein is a pharmaceutical composition, comprising the composition of the invention and a pharmaceutically acceptable carrier.

In another aspect of the invention, provided herein is a method for treating a medical condition, comprising administering the pharmaceutical composition of the invention to a subject in need thereof, thereby treating the medical condition.

In one embodiment, the method further comprises applying an acoustic wave to the subject, thereby generating reactive oxygen species.

In another aspect of the invention, provided herein is a process of manufacturing the particle of the invention, comprising the steps of:

providing an amphiphilic copolymer comprising a first block and a second block, wherein the second block has a solubility greater than the first block;

mixing the amphiphilic copolymer with a first solvent to form a first solution;

mixing an organometallic precursor with a second solvent, thereby forming a complex;

aging the complex, thereby forming a cluster;

mixing the first solution with the cluster thereby forming a mixture;

adding an aqueous solution to the mixture, thereby forming the particle.

In one embodiment, the aging comprises incubating the complex with the second solvent at a temperature ranging from 10 to 100° C., for a time period ranging from 1 to 40 days.

In one embodiment, the cluster is characterized by NMR.

In one embodiment, the mixing further comprises adding a hydrophobic compound, thereby obtaining the hydrophobic compound encapsulated within the particle.

In one embodiment, the process further comprises freeze-drying and/or spray-drying the particle to obtain a dry particle.

In one embodiment, the second solvent has a water content of less than 1% w/w.

In one embodiment, the second solvent is selected from the group comprising an aldehyde and a ketone.

In one embodiment, the aging predetermines a size of the particle.

In one embodiment, the metal oxide is a transition metal oxide.

In one embodiment, the organometallic precursor comprises a transition metal alkoxide.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description together with the drawings makes apparent to those skilled in the art how embodiments of the invention may be practiced.

In the drawings:

FIG. 13 A presents HR-SEM micrographs of hybrid $TiO_2$/T1107 nanoparticles produced with complexes aged between 1 and 36 days. Data collected with EDS detector. FIG. 13 B presents HR-SEM micrograph of $TiO_2$ nanoparticles obtained with a 20-day complex. Data collected by in-lens detector. The magnification in all the micrographs is 100,000× and the scale bar=1 um.

FIG. 14 A presents a micrograph of $TiO_2$ nanoparticles. FIG. 14 B presents a HR-SEM micrograph of hybrid $TiO_2$/T1107 nanoparticles. Data collected by in-lens detector. The magnification is 100,000× and the scale bar=100 nm.

DETAILED DESCRIPTION OF THE INVENTION

Figure 1:
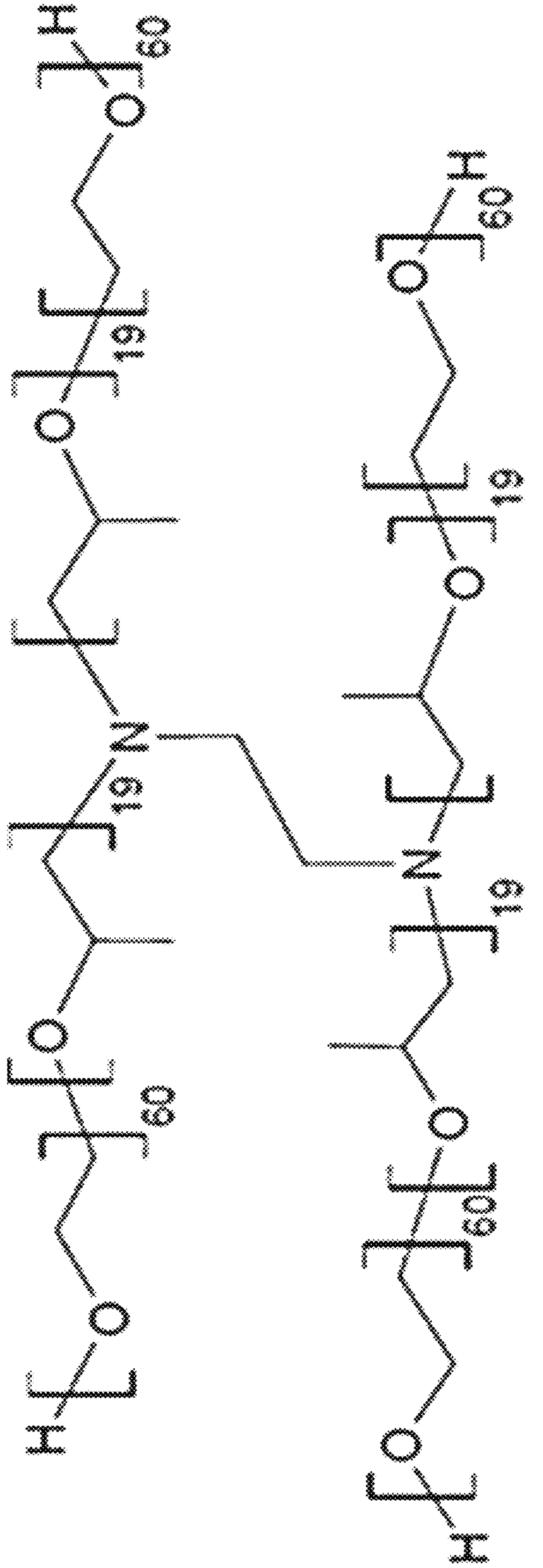
FIG. 1 presents a structure of T1107 (amphiphilic PEG-PPG copolymer).

In one aspect of the invention, provided herein is a particle comprising (i) an amphiphilic copolymer comprising a first block forming a hydrophobic core, and a second block having a water solubility greater than the first block; and (ii) a transition metal oxide;

wherein the transition metal oxide is bound to the second block, thereby forming a hydrophilic shell.

Amphiphilic Polymer

In some embodiments, there is provided a particle comprising one or more amphiphilic polymers. In some embodiments, one or more amphiphilic polymers comprise a hydrophobic block and a hydrophilic block. In some embodiments, one or more amphiphilic polymers are configured to form a multi-micellar structure in an aqueous solution.

In some embodiments, one or more amphiphilic polymers are copolymers. In some embodiments, one or more amphiphilic polymers comprise a first block forming a hydrophobic core, and a second block having a water solubility greater than the first block. In some embodiments, the first block is a hydrophobic block and the second block is a hydrophilic block.

In some embodiments, each of the hydrophobic block and the hydrophilic block comprises a polymeric chain having a plurality of monomeric units. In some embodiments, one or more amphiphilic polymers are block copolymers. In some embodiments, one or more amphiphilic polymers are graft copolymers. In some embodiments, the copolymers are random polymers. In some embodiments, the copolymers are branched polymers.

In some embodiments, the polymeric chain of the hydrophobic block is attached to the polymeric chain of the hydrophilic block. In some embodiments, the polymeric chain of the hydrophobic block is attached to the side chain of the hydrophilic block. In some embodiments, the polymeric chain of the hydrophilic block is attached to the side chain of the hydrophobic block. In some embodiments, the amphiphilic block or graft copolymers (referred to as "block") may form a structure having a hydrophobic core and a hydrophilic corona. In some embodiments, the amphiphilic block or graft copolymers may form various hydrophobic blocks and various hydrophilic blocks, wherein at least a portion of the hydrophilic block is capable of binding a cell receptor and/or transporter expressed at the outer surface of the cellular membrane. In some embodiments, at least a portion of the hydrophilic block is attached to a biologically active molecule, such as gene controlling moiety (e.g. antisense oligonucleotides). In some embodiments, at least a portion of the hydrophilic block is attached to a ligand capable of complex formation with a metal and/or metal cation suitable for imaging.

In some embodiments, at least a portion of the hydrophilic block is attached to a radioactive isotope, suitable for imaging.

By "attached to", also referred to herein as "grafted to", it is meant to refer to covalently and/or non-covalently bound, conjugated, hybridized, or immobilized.

In some embodiments, the hydrophobic blocks are configured to form a hydrophobic core and the hydrophilic blocks are configured to form a hydrophilic corona.

In some embodiments, the hydrophobic blocks are configured to form a plurality of hydrophobic blocks and the hydrophilic blocks are configured to form a plurality of hydrophilic blocks.

As used herein throughout, the term "polymer" describes an organic substance composed of a plurality of repeating structural units (backbone units) covalently bound to one another.

Herein throughout, the term "monomer" refers to a molecule that may bind chemically to other molecules to form an oligomer or a polymer.

The term "monomeric unit" refers to the repeating units, derived from the corresponding monomer. The terms "repeating unit" and "monomeric unit" are used herein throughout interchangeably. The polymer comprises the monomeric units. By "derived from" it is meant to refer to the polymeric compound following the polymerization process.

The term "amphiphilic polymer" is understood to mean a polymer which comprises at least a hydrophilic part (the term "part" is also referred to herein throughout as "block", "block" or "component", interchangeably) and at least a hydrophobic part, wherein the hydrophilic part has an aqueous solubility greater than the hydrophobic part.

The amphiphilic polymer is soluble or dispersible in an aqueous solution (e.g. water), directly or e.g., by means of pre-dissolution in an organic solvent miscible with an aqueous solution or a solvent that may be eliminated before redispersion of the amphiphilic polymer in an aqueous solution.

The amphiphilic copolymer is characterized by self-assembly in an aqueous solution, thus forming micellar structures as described herein below.

Typically, but not exclusively, the terms "hydrophilic block", and "hydrophilic block" may be understood to mean a polymer which, when introduced into an aqueous solution at a concentration of at least 1%, by weight, results in a macroscopically homogeneous solution.

The terms "hydrophilic", "soluble in an aqueous solution", and "dispersible in an aqueous solution" are used herein throughout interchangeably.

The terms "hydrophilic" and "hydrophobic" may be used herein, to assign the relative aqueous solubility of the polymeric block or block. In some embodiments, the hydrophilic block is more soluble in an aqueous solution than the hydrophobic block. In some embodiments, both hydrophobic and hydrophilic block when introduced into an aqueous solution at a concentration equal to 5%, by weight, result in a macroscopically homogeneous solution.

In some embodiments, the hydrophilic block has a greater aqueous solubility than the hydrophobic block. In some embodiments, the aqueous solubility of the hydrophilic block is greater, than the aqueous solubility of the hydrophilic block by at least 10%, at least 20%, at least 40%, at least 60%, at least 80%, at least 100%, at least 150%, at least 200%, at least 300%, at least 400%, at least 500%, at least 1000%, including any range/or value therebetween.

In some embodiments, the hydrophobic block is substantially insoluble in an aqueous solution. In some embodiments, the aqueous solubility of the hydrophobic block is less than less than 1% w/w, less than 0.5% w/w, less than 0.1% w/w, less than 0.01% w/w, less than 0.001% w/w, including any range or value therebetween.

In some embodiments, the amphiphilic polymer is characterized by hydrophilic-lipophilic-balance (HLB) value, as described herein below.

The term "block copolymer" refers to copolymers wherein monomeric units of a given type are organized in blocks, i.e. monomeric units of the same type are adjacent to each other. To explain further, the term "block copolymer" includes molecules of the type $Al_iB_jA_k$, wherein A and B designate distinct types of monomers and the indices i, j, k and 1 are integer numbers having a value of at least 1.

The term "amphiphilic block copolymer" according to some embodiments of the present invention designates block copolymers, comprising of a hydrophobic part and a hydrophilic part, wherein either or both parts may be made of one or more types of monomeric units, the monomeric units being organized in blocks. For example, the term "amphiphilic block copolymer" may relate to di-block copolymers of the general formula $A_iB_j$, wherein one of $A_i$ or $B_j$ is a hydrophobic polymer and the respective other moiety is a hydrophilic polymer.

The term "amphiphilic copolymer" according to some embodiments of the present invention designates block copolymers, comprising of a hydrophobic block(block) and a hydrophilic block(block), wherein both blocks may be made of one or more types of monomeric units, the monomeric units being organized in blocks.

The term "graft copolymer" refers to a copolymer having a backbone or main chain, side chains of different chemical groups at different positions connected along the backbone to the backbone or main chain. The side chains can be incorporated at different positions along the backbone by covalent attachment, to form the graft copolymer.

The polymers employed in the context of the present invention can thus be, in some embodiments, block (or multiblock) or graft copolymers comprising, for example, hydrophilic blocks alternating with hydrophobic blocks.

In some embodiments, the amphiphilic copolymer is cross-linked. In some embodiments, the polymer is post synthetically cross-linked, e.g. by a photo-induced cross-linking, or via non-covalent cross-linking (e.g. cation based cross linking). In some embodiments, the polymer is cross-linked during the synthesis step.

Such covalent cross-linking techniques are known in the art and may comprise connecting or networking cross-linkable polymeric chains by reacting them with short spacers. Such spacers may be short (e.g. less than 100 carbon atoms) aliphatic and/or alkylic chains having reactive groups on its distinct ends. Such reacting groups have to be compatible with reactive groups on the cross-linkable polymeric chains (e.g. both spacer and polymers having vinyl bonds; the polymer has amino groups and the spacer is a di-haloalkyl, or a di-isocyanate, etc.).

Polymeric chains may be non-covalently cross-linked, such as by ionic cross-linking. Various ionic cross-linkers and polymers suitable for ionic cross-linking are known in the art, including alginate cross-linked by divalent metal cations ($Ca^{2+}$, $Mg^{2+}$), etc.

In some embodiments, the hydrophilic block is at least partially cross-linked. In some embodiments, the hydrophobic block is at least partially cross-linked. In some embodiments, at least partially cross-linked amphiphilic polymer has an enhanced ability to self-assemble in an aqueous solution. In some embodiments, at least partially cross-linked amphiphilic polymer has an enhanced ability to form micelle-like structures in an aqueous solution. In some embodiments, at least partially cross-linked amphiphilic polymer has an enhanced and/or improved micelle-forming capability as compared to a non-crosslinked amphiphilic polymer.

In some embodiments, two or more hydrophobic blocks of the amphiphilic polymer are crosslinked, thereby stabilizing the hydrophobic core. In some embodiments, the hydrophobic core of at least partially cross-linked amphiphilic polymer, substantially retains its structural stability in an aqueous solution. In some embodiments, at least partially cross-linked amphiphilic polymer substantially remains in a micelle-like form within an aqueous solution.

Hydrophilic Block

In some embodiments, the hydrophilic block comprises a substantially water-soluble polymer. In some embodiments, the hydrophilic block comprises a plurality of water-soluble polymers.

Non-limiting examples of water-soluble polymers include but are not limited to: a polyether, a polysaccharide, a polyester, a polyphosphoester, a polyanhydride, a polyamide, a polyacrylamide, a polyacrylate, a polymetacrylate, a polyvinyl alcohol, a poly(oxazoline), a polypeptide or any combination thereof.

Further non-limiting examples of hydrophilic polymers may be e.g., natural, synthetic or semisynthetic polyols, polycarboxylic acids, polysulfates, polyamines, poly(cyclodextrins), or any combination thereof.

In some embodiments, the hydrophilic block comprises a water soluble polysachharide. In some embodiments, the water soluble polysachhcaride comprises a plurality of sugar-based monomers.

Mention may be made, by way of example and without being limited thereto, of the following sugar-based monomers and their salts which are capable of being employed to form the hydrophilic block, alone or in the form of a mixture thereof: alginate, galactomannan, hydrolyzed galactomannan, glucomannan, hydrolyzed glucomannan, guar gum, xanthan gum, pectin, cellulose, nanocrystalline cellulose, dermatan sulfate, cyclodextrins, poly(cyclodextrins), dextran, dextrin, starch, hyaluronic acid, chondroitin 4-sulfate, chondroitin 6-sulfate, heparin, heparan sulfate, keratin sulfate, beta-glucan, fucoidan, mannan, fucomannan, galactofucan, glucofucan and levan.

In some embodiments, the hydrophilic block is at least partially biodegradable and/or biocompatible.

In some embodiments, the hydrophilic block comprises a water-soluble polyether.

Non-limiting examples of a water-soluble polyether include but are not limited to: polyethyleneglycol (PEG).

In some embodiments, the polyether comprises one or more monomeric units having linear, branched, and/or substituted alkyl chain. In some embodiments, a substituted alkyl chain comprises one or more functional groups.

As used herein, functional groups, include, but are not limited to, a hydroxyl group, an amine group, a thiol group, a carboxyl group, a keto group, a sulfate group, a double or triple bond group, or any other reactive functional group, and combinations thereof.

In some embodiments, the substituted alkyl chain provides enhances hydrophilicity to the polymer. In some embodiments, the substituted alkyl chain comprises reactive groups providing the polymer a cross-linking ability.

In some embodiments, the hydrophilic polymer is conjugated to a bioactive moiety. In some embodiments, the hydrophilic polymer is conjugated to a bioactive moiety via a terminal hydroxyl group. In some embodiments, the hydrophilic polymer is conjugated to a bioactive moiety via the substituted alkyl chain.

In some embodiments, the hydrophilic block is conjugated to a molecule which is suitable for use in imaging (e.g. metal and/or metal cation, radionuclide, fluorescent probe, etc.).

In some embodiments, the hydrophilic block of the amphiphilic copolymer comprises a multifunctional polymer.

In some embodiments, the hydrophilic block of the amphiphilic copolymer is selected from natural, modified natural, synthetic or semisynthetic polymers.

In some embodiments, the hydrophilic block may have an average molecular weight (MW) of e.g., between 200 g/mol and 200,000 g/mol. In some embodiments, the MW of the hydrophilic block is from 500 to 100,000 g/mol, from 1000 to 50,000 g/mol, from 1000 to 40,000 g/mol, from 1000 to 30,000 g/mol, from 1000 to 20,000 g/mol, from 1000 to 10,000 g/mol, from 1000 to 5,000 g/mol, from 1000 to 3,000 g/mol, from 50,000 to 70,000 g/mol, from 70,000 to 100,000 g/mol, from 100,000 to 200,000 g/mol, including any range and/or value therebetween.

Hydrophobic Block

In some embodiments, the hydrophobic block is as described hereinabove.

In some embodiments, the term "hydrophobic block" is understood to mean blocks which are soluble or dispersible in fatty substances which are liquid at ambient temperature (e.g., 25° C.) or oils, such as alkanes, esters, ethers, triglycerides, silicones or fluorinated or other halogenated compounds or a mixture of hydrophobic materials (oils).

In some embodiments, the hydrophobicity characteristic of the block is unchanged regardless of temperature (e.g., 20° C. to 40° C.). In some embodiments, the hydrophobicity characteristic of the block is maintained at a defined range of temperature (e.g., 20° C. to 40° C.).

In some embodiments, the hydrophobicity characteristic of the block is unchanged regardless of the pH (e.g., 5 to 9). In some embodiments, the hydrophobicity characteristic of the block is maintained at a defined range of pH (e.g., 5 to 9).

In some embodiments, the hydrophobic block may comprise a substantially water insoluble compound selected from the group consisting of: a polyether (e.g., polypropylene glycol (PPG), polytetramethylene glycol (PTMG) and polybutylene glycol (PBG)), a polyacrylate (e.g., poly(methyl acrylate)), a polylactic acid (e.g., poly(D,L-lactide)), a polyglycolic acid, a polyglycolate ester, a polystyrene, a polycaprolactone (e.g., poly(epsilon-caprolactone) (PCL)), a phospholipid, and a fatty acid, or any derivative or copolymer thereof (e.g., poly(butylene oxide) (PBO) and poly(propylene glycol) (PPG) block co-polymers).

In some embodiments, the polymer is thermo-responsive polymer characterized by a defined lower critical solution temperature (LCST). For example, copolymers of N-isopropylacrylamide (NIPAAm) and acrylamide (AAm) exhibit a LCST that is slightly below body temperature (30-35° C.). Below the LCST the polymer undergoes hydration and thus it is water-soluble, whereas above the LCST hydrophobic interactions begin to appear, followed by de-hydration and shrinkage.

In some embodiments, the hydrophobic block is a block with at least two repeating units of any polyester, polyether, polycarbonate, polyanhydride, polyamide, polyacrylate, polymethacrylate, or any other hydrophobic homopolymer or heteropolymer, or a mixture thereof or any hydrophobic molecule of a group of fatty acids, fatty alcohols, or any other lipid molecule with at least two carbons in the backbone that may be grafted to the hydrophilic multifunctional polymer through the reactive functional groups.

In some embodiments, the hydrophobic block comprises a polymer suitable for non-covalent binding of a hydrophobic compound. In some embodiments, the hydrophobic block encapsulates a hydrophobic compound. In some embodiments, the hydrophobic compound is as described hereinbelow.

In some embodiments, the hydrophobic block comprises a substantially water-insoluble polyether. In some embodiments, the hydrophobic block is selected from the group consisting of: a linear PPG, a branched PPG, and a substituted PPG. In some embodiments, substantially is as described hereinabove.

In some embodiments, the hydrophobic block is at least partially biodegradable and/or biocompatible.

In some embodiments, the molar mass of the hydrophobic block is between 100 g/mol and 10,000 g/mol. In some embodiments, the molar mass is between 200 g/mol and 5,000 g/mol, between 1000 g/mol and 5,000 g/mol, between 1500 g/mol and 3,000 g/mol.

Self-Assembly Amphiphilic Polymers

As noted hereinabove, the hydrophilic blocks may form a plurality of hydrophilic blocks. As further noted hereinabove, the hydrophobic blocks may form a core structure or form various hydrophobic blocks.

In some embodiments, the hydrophobic blocks of the amphiphilic copolymer are cross-linked. Such cross-linked polymeric structure may be as exemplified by FIG. 1.

In some embodiments, the hydrophobic block is in the range of 10% to 90%, by weight, of the amphiphilic block copolymer.

In some embodiments, the amphiphilic copolymer is characterized by a hydrophilic-lipophilic balance (HLB) value that ranges from 1 to 24.

In some embodiments, the amphiphilic copolymer is characterized by a HLB value that ranges from 4 to 15. In some embodiments, the amphiphilic copolymer is characterized by a HLB value that ranges from 1 to 24, from 10 to 24, from 12 to 20.

In some embodiments, the amphiphilic copolymer is characterized by an average molecular weight (MW) ranging from 5000 to 1,000,000 g/mol, from 5000 to 100,000 g/mol, from 5000 to 20,000 g/mol, from 10,000 to 20,000 g/mol, from 20,000 to 100,000 g/mol, from 100,000 to 200,000 g/mol, from 200,000 to 300,000 g/mol, from 300,000 to 400,000 g/mol, from 400,000 to 500,000 g/mol, from 500,000 to 1,000,000 g/mol, from 20,000 to 40,000 g/mol, from 40,000 to 60,000 g/mol, from 60,000 to 80,000 g/mol, from 80,000 to 100,000 g/mol.

In some embodiments, the amphiphilic copolymer is characterized by a glass transition temperature ($T_g$) ranging from −60 to 200° C., from 0 to 100° C., from 10 to 80° C.

As noted hereinabove, the amphiphilic copolymer may self-assemble in an aqueous solution, thus forming a micelle-like structure.

The terms "self-assembled", or "self-aggregated", refer to a resulted structure of a self-assembly process based on a series of associative chemical reactions between at least two chemical blocks or polymers, which occurs when the associating groups on one chemical blocks or polymers are in sufficient proximity and are oriented so as to allow constructive association with another block or polymer. In other words, an associative interaction means an encounter that results in the attachment of the blocks or the polymers to one another.

As in all associative chemical reactions, the formation of a bond occurs between two groups within compounds or compositions depending on sufficient proximity there between. In the context of some embodiments of the present embodiments, the degree of sufficient proximity depends on the attractive forces that can be exerted by the associating groups and the relative reactivity thereof.

The phrase "attractive force", as used herein, refers to physical forces that span and have an effect over a distance, or field, such as electric and magnetic fields. Associating groups which can exert an attractive force field may attract each other over a definable distance, such as in the case of atoms having electrostatic charges.

The term "proximity" as used herein therefore describes any distance that allows interaction between such associating groups, whereby this distance can be practically null and depends on the presence, type and extent of the attractive forces which can be exerted by and affect the associating groups.

A pair of associating groups on two monomeric units or blocks should also be oriented appropriately so as to allow a constructive encounter there between which results in the formation of a chemical bond. This is particularly important in cases where the associating groups are characterized by radial asymmetry, directivity, polarity, dipole, vectorial force, effective angle and/or other directional and spatial characteristics. An appropriate orientation is determined by steric constrains, surface accessibility and other structural complementarity considerations as described hereinabove. The term "orientation" therefore refers to a steric location and directionality of an object with reference to another object (herein the associating groups).

Regardless if the associating groups exert an attractive force field which extends beyond the physical boundary of the monomeric units or blocks, or the degree of mutual reactivity of the associating groups, the monomeric units or blocks must be subjected to suitable conditions which will allow them to associate there between. By suitable conditions it is meant that the monomeric units or blocks need to be present at an adequate density (concentration) and possess suitable kinetic energy (temperature) so as to produce a sufficient number of events in which the monomeric units or blocks come in contact in the chemical sense, interact and associate (joined together). By "interact" it is meant that one or more monomeric units or blocks, each having associating groups thereon, while being subjected to suitable conditions as discussed herein below, can come close enough to one another, and at a certain angle range, so as to allow the associating groups to be attached to one another and/or to self-assemble.

In addition to an adequate concentration and suitable temperature, the condition which allows the self-assembly of a chemical structure includes other factors which affect the chemical environment in which the monomeric units or blocks are placed. These factors include the type of medium (solvent), the ionic strength and pH of the medium (solutes and buffers) and the presence of other chemical agents such as catalysts, oxidation and reduction agents, and other factors which may affect the reactivity of the associating groups.

Closed, hollow and self-assembled chemical structures as described herein below ("self-assembled core-shell structures" or "self-assembled multi-micellar structures") may be used in a myriad of applications, owing to several of the following most consistent and unique characteristics, such as:

- capacity to assemble and optionally disassemble under particular chemical and physical conditions;
- hollow and closed interior;
- uniform and reproducible distribution of shape, size and composition;
- defined (e.g. spherical, disc, cylindrical) overall shape; and
- wide range of controllable sizes.

One of the most intuitive uses of a closed and hollow molecular core that can reversibly self-assemble is a vehicle for substance (e.g a hydrophobic compound retention, and subsequent release thereof in or to a chemical, biological or physiological environment), as described herein below.

As mentioned hereinabove, in some embodiments, the amphiphilic copolymer is in form of a closed, e.g., hollow, and self-assembled structure, the structure having a hydrophobic core and a hydrophilic shell. In some embodiments the hydrophilic shell (corona) interacts with an aqueous solution, thus stabilizing the self-assembled structure in the solution. In some embodiments water molecules, and optionally ionic species, form non-covalent interactions with the hydrophilic shell, resulting in a non-covalently cross-linked polymeric matrix.

In some embodiments, the particle comprises a plurality of self-assembled amphiphilic copolymers. In some embodiments, the plurality of the amphiphilic copolymers is self-assembled.

In some embodiments, a plurality of amphiphilic block or graft copolymers described herein forms a micelle, a micelle-like, a core-shell structure, or a multi-micellar structure.

As used herein, the term "micelle" describes a colloidal particle, in a simple arrangement or geometric form, typically spherical, of a specific number of amphiphilic molecules, which forms at a well-defined concentration, called the critical micellar concentration (CMC). The micelle can be a single particle or can be formed by a cluster of several micelles, which interact with one another so as to form a particle having a larger dimension (referred to as "multi-micellar particle").

The phrase "critical micellar concentration" (CMC) describes the concentration of the disclosed amphiphilic block copolymers above which the amphiphilic copolymers are present substantially in a micellar form under a given set of conditions. At the vicinity of CMC, sharp change in many experimental parameters may be observed, and this may be measured by a number of techniques that include, but not limited to, surface tension measurements, fluorescence, light scattering, conductivity, osmotic pressure, and the like CMC varies as a function of a number of physical factors such as pH, temperature, ionic strength and pressure.

In some embodiments, the disclosed amphiphilic copolymer or a plurality thereof form a closed, e.g., hollow, and self-assembled structure e.g., micelle or a micelle-like structure. That is, each self-assembled structure comprises at least e.g., 1, 2, 3, 4, 5, 6, 7, 8, 9, 10, 11, 12, 13, 15, 16, 17, 18, 19, 20, 30, 40, 50, 60, 70, 80, 90, 100, 1000, 10,000, or at least 100,000 amphiphilic copolymers.

As used herein, the terms "corona", or "shell", which are used herein throughout interchangeably, refer to the sphere (typically the hydrophilic block(s)) surrounding the core. The term "sphere" is used only for the purpose of illustration and it is to be construed that is not only limited to spherical shape but also includes any shape which may find suitability to at least some embodiments of the present invention.

The term "core" refers to the central region (typically the hydrophobic block(s)) of the structure, which typically contains the hollow.

The term "hydrophilic block" may refer to zones in the particle that contain mainly (e.g., at least 60% or at least 70%) the hydrophilic block of the polymer.

The term "hydrophobic block" may refer to zones in the particle that contain mainly (e.g., at least 60% or at least 70%) the hydrophobic blocks of the polymer.

The term "closed" as used herein, is a relative term with respect to the size, the shape and the composition of two entities, namely an entity that defines an enclosure (the enclosing entity) and the entity that is being at least partially enclosed therein. In general, the term "closed" refers to a morphological state of an object which has discrete inner and outer surfaces which are substantially disconnected, wherein the inner surface constitutes the boundary of the enclosed area or space. The enclosed area or space may be secluded from the exterior area of space which is bounded only by the outer surface.

In the context of the present invention, the closure of the enclosing entity depends of the size, shape and chemical composition of the entity that is being enclosed therein, such that the enclosing entity may be "closed" for one entity and at the same time be "open" for another entity. For example, structures presented herein are closed with respect to certain chemical entities which cannot pass through their enclosing shell or corona, while the same "closed" structures are not closed with respect to other entities.

For example, the structures of the present embodiments may be closed with respect to, for example, a drug molecule, but non-closed with respect to, for example, a single atom ion or an atom of a noble gas. In the context of the present invention, the same "closed" structures are affected by certain conditions e.g., pH, temperature, concentration, etc.

The terms "hollow" or "hollow sphere" is used only for the purpose of illustration and it is to be construed that is not only limited to spherical shape but also includes any shape which may find suitability to at least some embodiments of the present invention, the same "closed" structures are affected by certain conditions e.g., pH, temperature, concentration, etc.

The term "hollow", as used herein, refers to an object having a vacuous cavity, a gap, a void space or an empty space enclosed within. The term "hollow" is not only limited to spherical shape but also includes any shape which may find suitability to at least some embodiments of the present invention. By "void space" herein it is meant to refer to a polymer-free space or a central cavity. The term hollow is used herein as an illustration and it is to be construed that the core-corona structure are not fully hollow in the core.

In some embodiments, the core or the various hydrophobic blocks are of e.g., spherical, cylindrical, rod, lamellae, irregular or any other morphology.

In some embodiments, once solubilized in water or in any other aqueous medium, and at a final concentration above a certain concentration and/or at certain range of temperature, the amphiphilic copolymer undergo self-aggregation to form nanoscopic, submicroscopic or microscopic structures.

In some embodiments, the amphiphilic copolymer comprises a multiblock of PEG-PPG copolymers. In some embodiments, the amphiphilic copolymer is a cross-linked PEG-PPG copolymer. In some embodiments, the amphiphilic copolymer is F1107, having a structure as exemplified by FIG. 1.

Non-limiting examples of PEG-PPG copolymers include, but not limited to: F127, P123 and T904. These triblock copolymers are configured of repeating PEG-PPG-PEG units and are characterized by varying PEG:PPG ratio within the copolymer. For example, P123 is represented by Formula: $HO(CH_2CH_2O)_{20}—(CH_2CH(CH_3)O)_{70}—(CH_2CH_2O)_{20}H$; F127 is represented by Formula: $HO(CH_2CH_2O)_{101}—(CH_2CH(CH_3)O)_{56}—(CH_2CH_2O)_{101}H$.

In some embodiments, the w/w ratio of the hydrophobic block to the hydrophilic block within the amphiphilic copolymer is in a range from 1 to 99%, from 10 to 50%, from 10 to 30%, from 20 to 30%, from 1 to 10%, from 50 to 90%, including any range therebetween.

In some embodiments, the amphiphilic copolymer is soluble in an aqueous solution. In some embodiments, the aqueous solubility of the amphiphilic copolymer ranges from 1 to 400 g/L.

In some embodiments, the amphiphilic copolymer is soluble in an organic solvent. In some embodiments, the solubility of the amphiphilic copolymer in an organic solvent ranges from 0.1 to 500 g/L.

Transition Metal Oxide

In another aspect, provided herein a hybrid particle comprising a transition metal oxide bound to the amphiphilic copolymer.

Non-limiting examples of transition metals include but are not limited to: iron (Fe), aluminum (Al), zinc (Zn), tungsten (W), titanium (Ti), silicon (Si), zirconium (Zr), hafnium (Hf), tin (Sn), gallium (Ga), molybdenum (Mo), nickel (Ni), vanadium (V), platinum (Pt), tantalum (Ta), germanium (Ge) and niobium (Nb) or any combination thereof.

Non-limiting examples of transition metal oxides include but are not limited to aluminum oxide, iron (II/III) oxide, zirconium oxide, titanium oxide, or a mixture thereof.

In some embodiments, transition metal oxides are characterized by their relative polarity. In some embodiments, transition metal oxides stabilize a dry particle.

In some embodiments, transition metal oxides are in a form of metal oxo-polymers within the particle. In some embodiments, transition metal oxides form a polymeric matrix. In some embodiments, metal oxo-polymers stably encapsulate a hydrophobic compound. In some embodiments, metal oxo-polymers are characterized by their porosity. In some embodiments, metal oxo-polymers are characterized by their high surface area.

As used herein, metal-oxopolymers are inorganic polymers comprising a di-, tri-, or tetra-coordinated metal bound to oxygen atoms, resulting in an amorphous network of polymeric chains. The polymeric chain of such metal-oxopolymers can be represented by a general formula 1:

$$-[M-O_m]_n—$$

wherein M is a metal (such as Al, Ti, Zr).

Metal-oxopolymers are usually synthesized starting from molecular metal oxide precursors, such as metal alkoxides (e.g. $Si(OEt)_4$, $Ti(OEt)_4$). The polymer chain formation occurs by inorganic polymerization reactions. Initiation is performed through the hydrolysis of alkoxy groups as follow: $M-(OR)_m+H_2O \rightarrow HO-M-(OR)_{m-1}+ROH$. As soon as hydroxy groups are generated, propagation occurs through a polycondensation process. Metal-oxopolymers are characterized by high porosity, and a large surface area.

In some embodiments, metal-oxopolymers are hydrolysable in an aqueous solution. In some embodiments, metal-oxopolymers are bio erodible under physiological conditions.

Particle

In another aspect of the invention, provided herein a particle comprising a hybrid material. As used herein, hybrid material refers to a composition comprising a metal oxide and an amphiphilic copolymer. In some embodiments, a w/w ratio of the transition metal oxide to the amphiphilic copolymer ranges from 10 to 90% within the particle.

In some embodiments, provided herein a hybrid particle comprising an amphiphilic copolymer and a metal oxide. In some embodiments, the amphiphilic copolymer is as described herein above. In some embodiments, metal oxide is titanium oxide ($TiO_2$). In some embodiments, titanium oxide is in a form of oxopolymer. In some embodiments, the particle comprises titanium (IV). In some embodiments, titanium oxide is mostly found in a tetrahedral conformation within the particle. In some embodiments, the particle comprises $TiO_2$ and PEG-PPG copolymer.

In some embodiments, the particle is in an amorphous state. In some embodiments, the metal-oxopolymer within the particle is in an amorphous state. In some embodiments, the particle is devoid of a crystalline metal oxide.

In some embodiments, the particle is a dry particle, comprising less than 10% w/w, less than 5% w/w, less than 3% w/w, less than 1% w/w, less than 0.1% w/w water.

In some embodiments, the particle is devoid of organic solvent. In some embodiments, the particle comprises less than less than 3% w/w, less than 1% w/w, less than 0.1% w/w, less than 0.01% w/w organic solvent.

Figure 4:
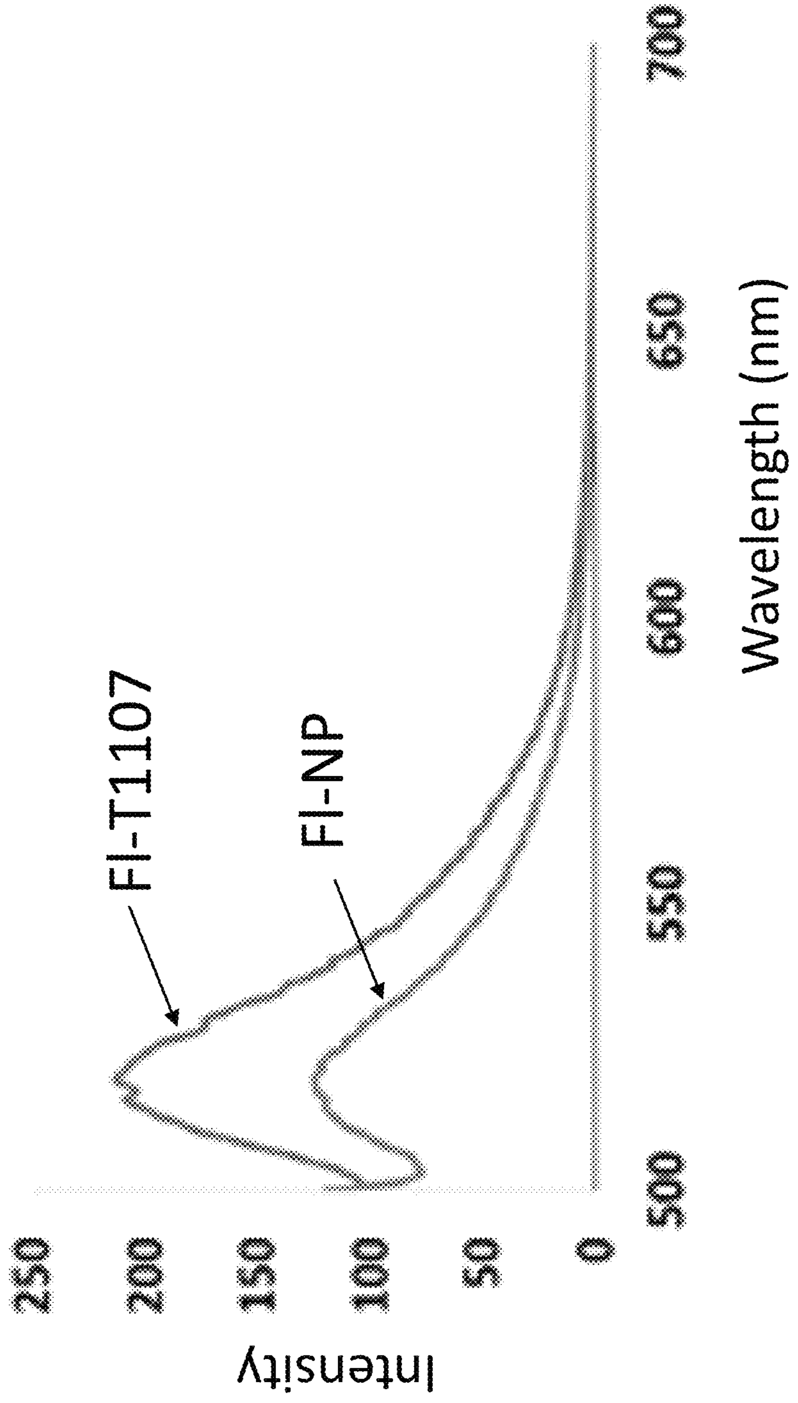
FIG. 4 presents emission spectra of fluorescein-labeled T1107 (Fl-T1107) and hybrid nanoparticles (Fl-NP). The fluorescein concentration was identical in both samples.
Figure 5A:
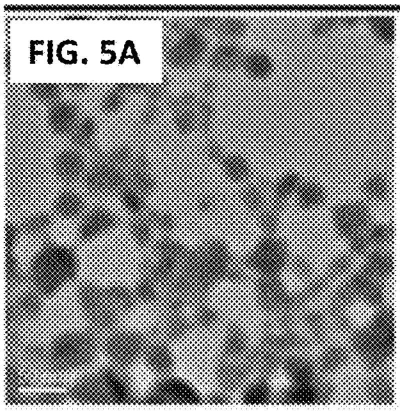
FIGS. 5A-G present micrographs of hybrid $TiO_2$/T1107 nanoparticles produced with a 20-day aged oxo-organo complex by TEM. (A, B) TEM in bright-field mode (Tecnai G2 T20 S-Twin, FEI) and (C-E) high-angle annular dark field-scanning transmission electron microscopy (HAADF-STEM) analysis (FEI Thermo Fisher Titan Cubed Themis G2 300). (D) yellow, (E) green and (F) red indicate the distribution of C, N, and Ti, respectively, in the nanoparticle bulk. (G) $TiO_2$ nanoparticles produced under the same conditions, though without the addition T1107 were used as control.
Figure 5B:
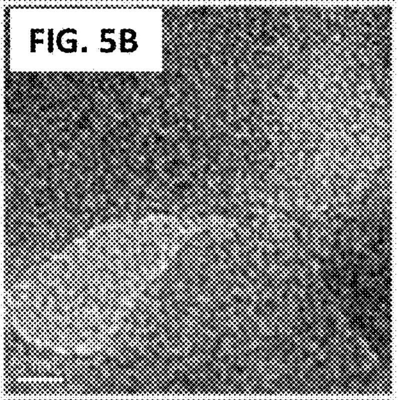
Figure 5C:
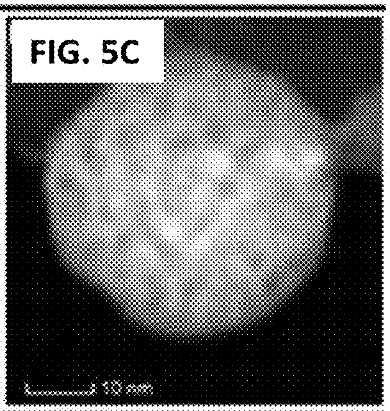
Figure 5D:
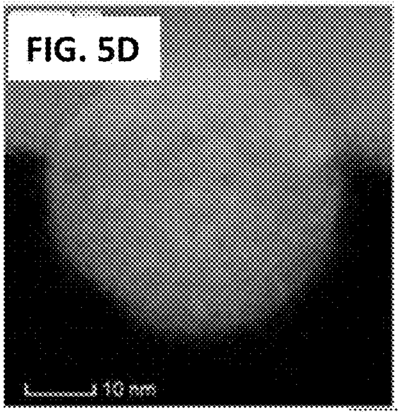
Figure 5E:
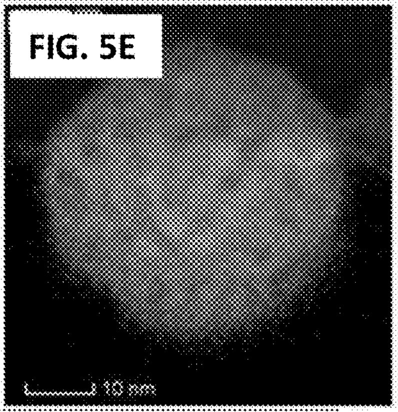
Figure 5F:
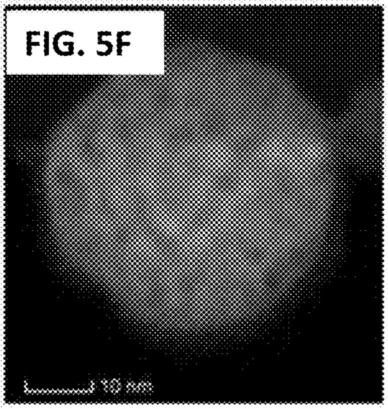
Figure 5G:
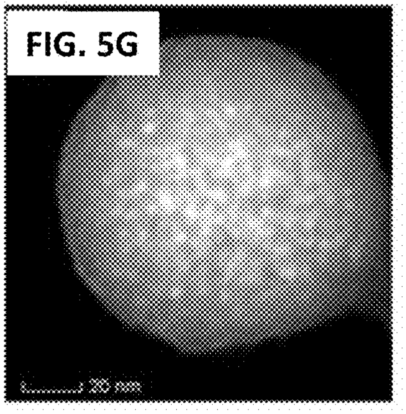

In some embodiments, the amphiphilic copolymer and metal oxide are substantially mixed within the particle. In some embodiments, the amphiphilic copolymer is substantially incorporated within a metal oxide matrix. These results are extensively supported by data provided in FIG. 4 showing a quenching of fluorescently labeled $TiO_2$ particles, and FIG. 5 showing a co-localization of Ti and N atoms in the nanoparticle.

In some embodiments, the particle comprises the metal-oxopolymer bound to the amphiphilic copolymer. In some embodiments, the particle comprises an amphiphilic copolymer forming a hydrophobic core and a hydrophilic shell, as described hereinabove.

In some embodiments, the hydrophilic shell comprises the metal-oxopolymer bound to the hydrophilic block of the amphiphilic copolymer. In some embodiments, the metal-oxopolymer forms non-covalent interactions with the hydrophilic block. In some embodiments, the metal-oxopolymer and the hydrophilic block are bound via dipole-dipole interactions. In some embodiments, the metal-oxopolymer and the hydrophilic block are bound via hydrogen bonds.

In some embodiments, the metal-oxopolymer stabilizes the particle. In some embodiments, the metal-oxopolymer encapsulates the amphiphilic polymer. In some embodiments, the metal-oxopolymer provides an inorganic matrix for the amphiphilic polymer. In some embodiments, the metal-oxopolymer provides a physical stability to the particle. In some embodiments, the metal-oxopolymer provides a physical stability to the particle in a solution and/or dispersion. In some embodiments, the metal-oxopolymer stabilizes the particle in an aqueous solution and/or dispersion. In some embodiments, the metal-oxopolymer prevents a dissociation of micellar structures formed by the amphiphilic polymer. In some embodiments, the metal-oxopolymer prevents a dissociation of micellar structures in solution.

In some embodiments, the metal-oxopolymer provides a chemical stability to the particle. In some embodiments, the metal-oxopolymer reduces degradation of the particle. In some embodiments, the metal-oxopolymer reduces bioerosion of the particle. In some embodiments, the metal-oxopolymer reduces a hydrolysis ratio of the particle.

As used herein throughout, the term "stable", or any grammatical derivative thereof, may refer to chemical stability. "Chemical stability" means that an acceptable percentage of degradation of the self-assembled structure disclosed herein throughout produced by chemical pathways such as oxidation or hydrolysis is formed. In particular, the self-assembled structure is considered chemically stable if no more than about 10% breakdown products are formed after e.g., two weeks of storage at the intended storage temperature of the product (e.g., room temperature, i.e. 15° C. to 30° C.).

The term "stable", or any grammatical derivative thereof, may also refer to physical stability. The term "physical stability" means that with respect to the self-assembled structure disclosed herein throughout, an acceptable percentage of aggregates (e.g., dimers, trimers and larger forms) remains formed. In particular, a formulation is considered physically stable if at least about 15% of the aggregates remain formed after e.g., two weeks of storage at the intended storage temperature of the product (e.g., room temperature).

The term "stable" may also refer to the active or therapeutic agent (as described herein below) encapsulated within the self-assembled structure, meaning that at least about 65% of therapeutic agent remains chemically and physically stable after e.g., one month of storage at room temperature.

In some embodiments, the amphiphilic polymer provides a template for particle formation. In some embodiments, a micellar structure of the amphiphilic polymer in solution provides a template for the particle formation. In some embodiments, the amphiphilic polymer being self-assembled in a form of a micellar structure, induces a formation of a globular-shaped particle. In some embodiments, the micellar structure of the amphiphilic polymer induces a formation of a core-shell particle.

In some embodiments, the amphiphilic polymer enhances thermal stability of the particle. In some embodiments, the amphiphilic polymer reduces thermal degradation of the particle.

In some embodiments, the hydrophobic block of the amphiphilic polymer forms the core, and the hydrophilic block of the amphiphilic polymer bound to the metal oxide forms the shell. In some embodiments, the hydrophilic block induces a formation of metal oxide layer within the hydrophilic shell of the particle. In some embodiments, the hydrophilic block induces a formation of the metal-oxopolymer within the hydrophilic shell of the particle.

In some embodiments, the hydrophilic block induces deposition of the metal-oxopolymers within the hydrophilic shell of the particle. In some embodiments, the hydrophilic block forms a hydrogel upon addition of water. In some embodiments, the hydrogel enhances binding to metal-oxopolymers. In some embodiments, the hydrogel binds to metal-oxopolymers via hydrogen bonds. In some embodiments, the hydrogel enhances the formation of metal-oxopolymers from metal oxide precursors. In some embodiments, the hydrogel catalyzes the polymerization of metal oxide precursors.

In some embodiments, the hydrophilic block stabilizes the particle in solution. In some embodiments, the hydrophilic block stabilizes the particle in dispersion. In some embodiments, the hydrophilic block enhances hydrogen bonds formation, thereby stabilizing the particle in an aqueous solution and/or dispersion. In some embodiments, the hydrophilic block enhances solubility of the particle. In some embodiments, the hydrophilic block enhances dispersibility of the particle. In some embodiments, the hydrophilic block reduces agglomeration of particles. In some embodiments, the hydrophilic block provides spacing units for metal-oxopolymer chains, thereby reducing agglomeration. In some embodiments, the hydrophilic block forms a layer on the outer surface of the particle. In some embodiments, agglomeration of particles in solution and/or dispersion is reduced by formation of PEG layer on the outer surface of the particle. In some embodiments, PEG layer on the outer surface of the particle interacts with surrounding water molecules, thereby enhancing the stability of the particle in solution.

In some embodiments, the amphiphilic polymer enhances a porosity of the particle. In some embodiments, the amphiphilic polymer enhances a particle load. In some embodiments, the amphiphilic polymer enhances an encapsulation capacity of the particle.

In some embodiments, the particle further comprises a hydrophobic compound bound to the hydrophobic core. In some embodiments, the hydrophobic compound is bound to the core via hydrophobic interactions. In some embodiments, a hydrophobic compound is encapsulated within the particle.

In some embodiments, the w/w concentration of the hydrophobic compound within the particle ranges from about 0.5% to 50%, from about 0.5% to 1%, from about 1% to 5%, from about 5% to 10%, from about 10% to 15%, from about 15% to 20%, from about 20% to 30%, from about 30% to 40%, from about 40% to 50%, including any value or range there between, by total dry weight of the particle.

In some embodiments, the composition comprises e.g., 0.5%, 1%, 1.5%, 2%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 20%, 30%, or about 40% of active agent, including any value and range there between, by total dry weight of the particle.

In some embodiments, the hydrophobic compound is stably encapsulated within the particle. In some embodiments, the hydrophobic compound retains its structural stability with the particle. In some embodiments, the hydrophobic compound retains its chemical activity upon encapsulation within the particle.

In some embodiments, the encapsulated hydrophobic compound is stable under physiological conditions. In some embodiments, the hydrophobic compound is stably encapsulated within the particle. In some embodiments, the hydrophobic compound remains stably encapsulated under physiological conditions for at least 1 hour, for at least 2 h, for at least 5 h, for at least 10 h for at least 15 h, for at least 20 h, for at least 24 h, including any range and/or value therebetween.

In some embodiments, the encapsulated hydrophobic compound hydrophobic compound substantially retains its activity. In some embodiments, the particle comprising an encapsulated hydrophobic compound prevents its degradation in vivo.

In some embodiments, the particle substantially releases its load (e.g. hydrophobic compound). In some embodiments, the particle releases at least 30%, at least 40%, at least 50%, at least 60%, at least 70%, at least 80%, at least 90%, at least 95% of its load. In some embodiments, the particle has a controlled release profile, as exemplified by FIG. 6. In some embodiments, the particle releases its load in a controlled manner.

In this context, the term "controlled manner" indicates that the load (e.g. active compound such as drug) is released substantially constantly, or in accordance with a pre-defined rate to e.g., a target cell. Herein, the term "constantly" may refer to a time duration of about e.g., 30 min, 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days, including any value there between.

In some embodiments, at least 10% of the particle load is released after 2 h. In some embodiments, at least 30%, at least 40%, at least 50% is released after 2 h under physiological conditions.

As used herein, the term "physiological conditions" or "physiological environment" refers to conditions of the external or internal milieu that may occur within an organism or cell system, in contrast to artificial laboratory conditions. A temperature range of 20-40° C., pH of 6-8, glucose concentration of 1-20 mM, atmospheric oxygen concentration, proteolytic and hydrolytic enzymes, endogenous reducing agents are examples of physiological conditions for most earth organisms The term "physiological conditions" may include, for example, hydrolysis (decomposition via hydrolytic cleavage), enzymatic catalysis (enzymatic degradation), and mechanical interactions.

Non-limiting examples of hydrophobic compounds include but are not limited to: a pharmaceutically active agent, a labeling agent, a diagnostic agent, a prophylactic agent, a surface-modifying agent, a nutraceutical, or any combination thereof.

In some embodiments, the hydrophobic compound is substantially water-insoluble. In some embodiments, the solubility of the hydrophobic compound is as defined hereinabove for the hydrophobic block.

In some embodiments, the particle retains its structural and chemical identity in a physiological environment for at least at least 1 hour, for at least 2 h, for at least 5 h, for at least 10 h, for at least 15 h, for at least 20 h, for at least 24 h, including any range and/or value therebetween.

In some embodiments, the particle is characterized as being substantially biodegradable. In some embodiments, the particle is characterized as being substantially biocompatible. In some embodiments, the metal oxopolymer is biodegradable and/or biocompatible. In some embodiments, the amphiphilic copolymer is at least partially biodegradable and/or biocompatible.

The term "biodegradable" as used in the context of embodiments of the invention, also encompasses the term "bioresorbable", which describes a substance that decomposes under physiological conditions to break down products that undergo bioresorption into the host-organism, namely, become metabolites of the biochemical systems of the host-organism.

The term "biocompatible" as used in the context of embodiments of the invention, describes a substance (such as a biomaterial), that performs its desired function, without eliciting any undesirable local or systemic toxicity effects in the host-organism.

In some embodiments, the particle is labeled by a labeling agent. In some embodiments, the labeling agent is incorporated within the particle. In some embodiments, the labeling agent is covalently bound to the particle. In some embodiments, the labeling agent is bound to the particle by a non-covalent bond. In some embodiments, the labeling agent is covalently bound to the hydrophilic block of the amphiphilic copolymer.

Non-limiting examples of labeling agents contain but are not limited to: a fluorophore (e.g. a fluorescent protein, a small-molecule fluorophore, a molecular beacon, FRET inducing molecule), an imaging probe (e.g. a radionuclide, an MRI probe, a CT probe, a PET probe, a SPECT probe), a photosensitizer (e.g. a probe for photodynamic therapy).

Figure 13A:
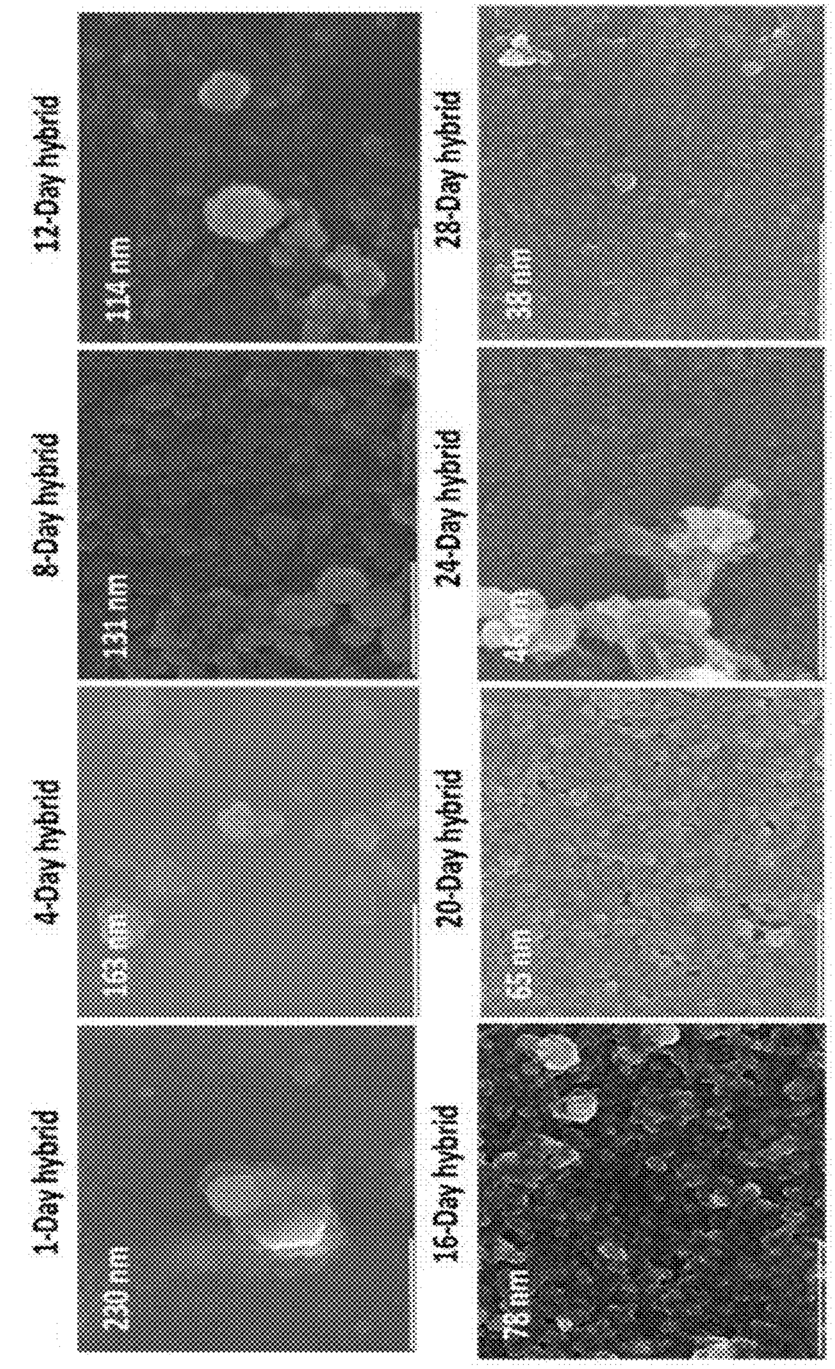
FIGS. 13 A-B present HR-SEM micrographs showing $TiO_2$ and hybrid $TiO_2$/T1107 nanoparticles produced by the aqueous-phase nanoprecipitation of Ti(IV) acetone oxo-organo complexes at different aging times.

In some embodiments, the particle is characterized by a globular shape (FIG. 13A).

In some embodiments, provided herein a composition comprising a plurality of particles. In some embodiments, the composition further comprises a suitable carrier. In some embodiments, a suitable carrier is as described hereinbelow.

In some embodiments, the plurality of particles is characterized by a particle size.

In some embodiments, the particle size ranges from 1 to 500 nm. In some embodiments, the particle size ranges from 1 to 30 nm. In some embodiments, the particle size ranges from 30 to 70 nm. In some embodiments, the particle size ranges from 30 to 100 nm. In some embodiments, the particle size ranges from 100 to 300 nm. In some embodiments, the particle size ranges from 400 to 500 nm. In some embodiments, the particle size ranges from 100 to 200 nm. In some embodiments, the particle size ranges from 100 to 150 nm. In some embodiments, the particle size ranges from 150 to 200 nm. In some embodiments, the particle size ranges from 200 to 350 nm. In some embodiments, the particle size ranges from 200 to 250 nm. In some embodiments, the particle size ranges from 250 to 300 nm. In some embodiments, the particle size ranges from 300 to 350 nm. In some embodiments, the particle size ranges from 350 to 400 nm, including any value or range therebetween.

In some embodiments, at least 70% of the particles are characterized by a particle size (also referred to herein throughout as "size" or "diameter") that ranges from 1 nm to 500 nm. In some embodiments, at least 80% of the particles are characterized by a diameter that ranges from 1 nm to 500 nm. In some embodiments, at least 90% of the particles are characterized by a diameter that ranges from 1 nm to 500 nm.

In some embodiments, the particle size is an average particle size. In some embodiments, the particle size is a hydrodynamic size of the particle in an aqueous solution. The hydrodynamic size of the particle can be determined by Differential Light Scattering (DLS) analysis.

In some embodiments, the particle is characterized by a predetermined size. In some embodiments, the particle size is predetermined by a composition of the particle. In some embodiments, the particle size is predetermined by a composition of the amphiphilic polymer. In some embodiments, the particle size is predetermined by a chemical composition of the amphiphilic polymer. In some embodiments, the particle size is predetermined by a configuration of blocks within the amphiphilic polymer.

Figure 7:
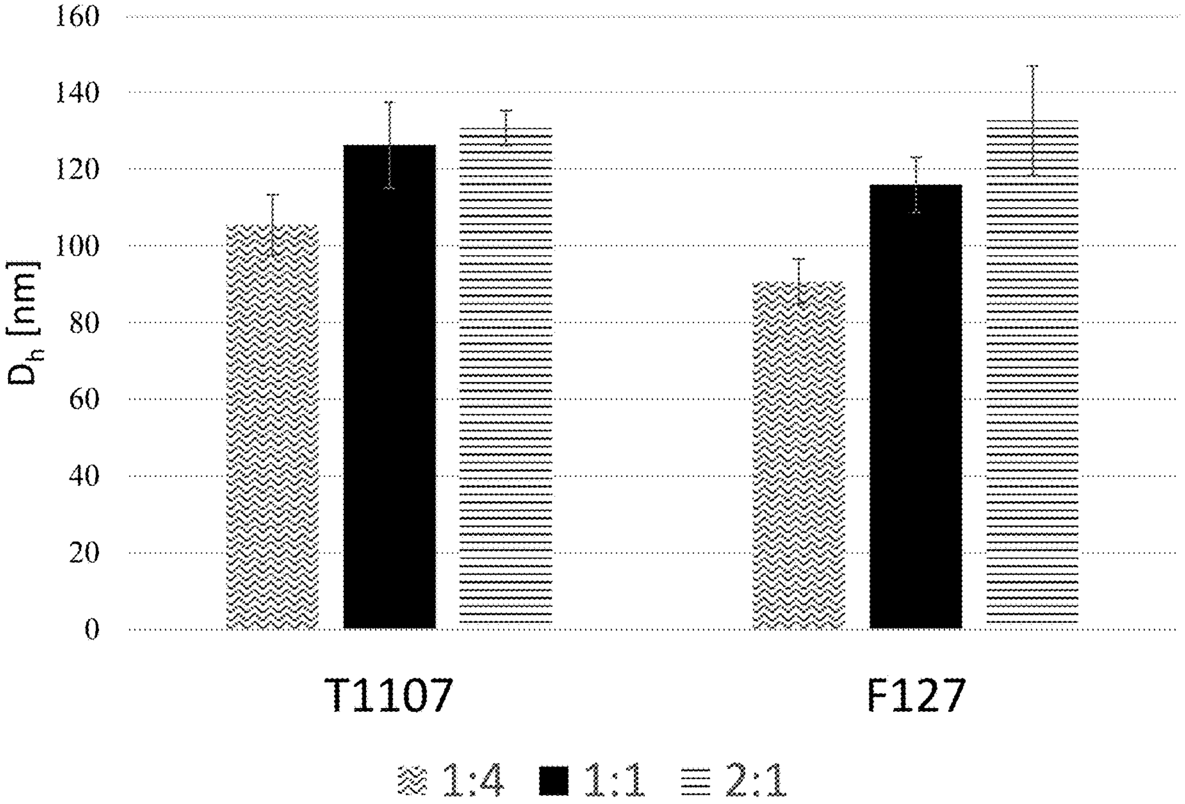
FIG. 7 presents a bar graph showing the particle size of hybrid $TiO_2$/T1107 and $TiO_2$/F127 nanoparticles at different volume ratios of the complex to the amphiphilic copolymer. A complex aged for 20 days was used for the experiment.
Figure 8:
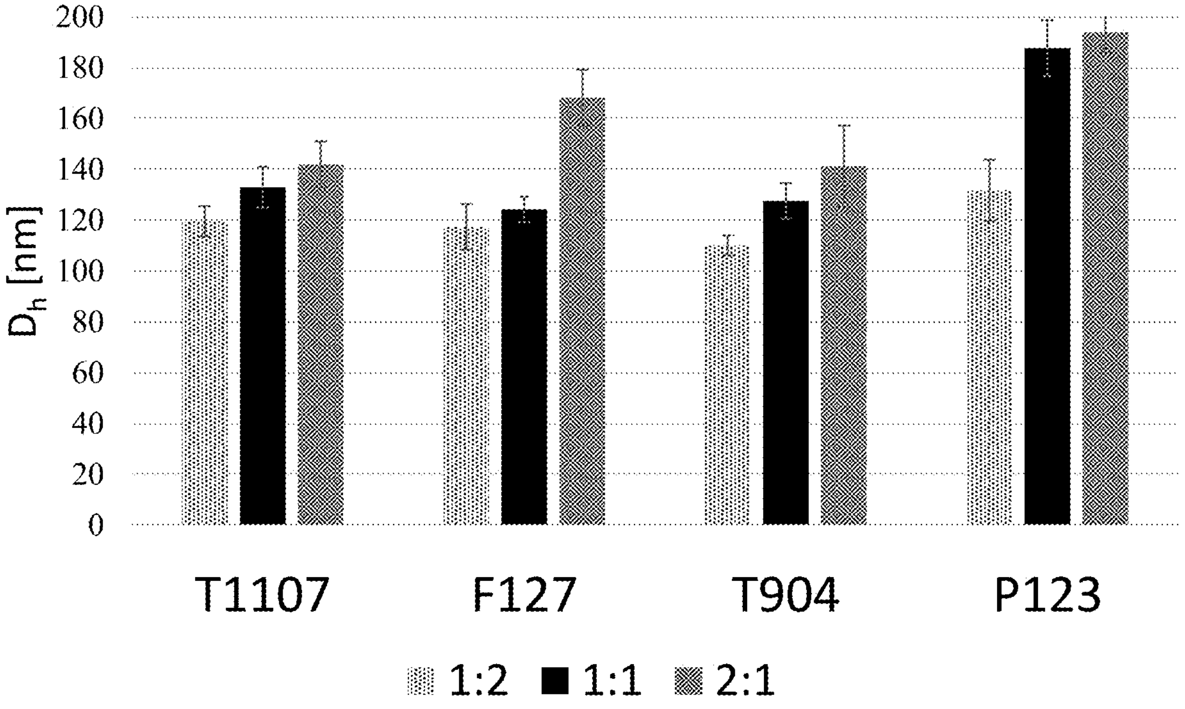
FIG. 8 presents a bar graph showing the particle size of hybrid $TiO_2$/T1107, $TiO_2$/F127, $TiO_2$/P123 and $TiO_2$/T904 nanoparticles at different volume ratios of the complex to the amphiphilic copolymer. A complex aged for 24 days was used for the experiment.

In some embodiments, the particle size is predetermined by a w/w ratio between the hydrophilic block and the hydrophobic block, as exemplified by FIG. 8, showing the particle size using copolymers with different w/w ratios of PEG:PPG. In some embodiments, the particle size is predetermined by a v/v ratio between the metal oxide and the amphiphilic polymer, as exemplified by FIGS. 7 and 8.

In some embodiments, increasing a hydrophilicity of the amphiphilic polymer results in the reduced particle diameter (FIG. 8).

In some embodiments, the particle diameter is predetermined by aging a complex, as described hereinbelow.

In some embodiments, a plurality of particles as disclosed herein is characterized by a narrow polydispersity index (PDI). In some embodiments, a plurality of particles is characterized by a PDI being in a range from 0.01 to 0.5, as exemplified by Table 1.

TABLE 1 size and size distribution of hybrid $TiO_2$/T1107 nanoparticles, as measured by DLS and HR-SEM.

| Complex age (Days) | DLS $D_h$ ± S.D. (nm) | DLS PDI ± S.D. | HR-SEM Average D ± S.D. (nm) |
|---|---|---|---|
| 1 | 228 ± 30 | 0.540 ± 0.087 | 230 ± 169 |
| 4 | 222 ± 20 | 0.387 ± 0.037 | 163 ± 73 |
| 8 | 218 ± 14 | 0.262 ± 0.017 | 131 ± 43 |
| 12 | 137 ± 8 | 0.0230 ± 0.013 | 114 ± 43 |
| 16 | 136 ± 8 | 0.232 ± 0.017 | 78 ± 12 |
| 20 | 128 ± 8 | 0.229 ± 0.034 | 65 ± 18 |
| 24 | 118 ± 4 | 0.200 ± 0.010 | 46 ± 9 |
| 28 | 73 ± 11 | 0.335 ± 0.145 | 38 ± 10 |

TABLE 1-continued size and size distribution of hybrid $TiO_2$/T1107 nanoparticles, as measured by DLS and HR-SEM.

| Complex age (Days) | DLS $D_h$ ± S.D. (nm) | DLS PDI ± S.D. | HR-SEM Average D ± S.D. (nm) |
|---|---|---|---|
| 32 | 64 ± 8 | 0.202 ± 0.056 | 30 ± 8 |
| 36 | 53 ± 6 | 0.281 ± 0.083 | 26 ± 6 |

In some embodiments, a plurality of particles is characterized by PDI ranging from 0.01 to 0.1, from 0.1 to 0.2, from 0.2 to 0.3, from 0.3 to 0.4, from 0.4 to 0.5, including any range or value therebetween.

In some embodiments, at least e.g., 50%, 60%, 70%, 80%, 90% or 99% of plurality of the disclosed amphiphilic block copolymers is characterized by a narrow PDI.

As used herein, "polydispersity index" (denoted herein throughout as: "PDI") refers to a measure of the distribution of particle diameters in a given sample. In DLS, the (absolute) standard deviation of the distribution can be compared to the mean, and a relative DLS-PDI=standard deviation/mean is obtained. For a theoretical Gaussian distribution, the overall polydispersity is the relative polydispersity of the distribution. Traditionally, this overall polydispersity has also been converted into an overall DLS-PDI which is the square of the light scattering polydispersity. For a perfectly uniform sample, the PDI value in the context of DLS would be about 0.

Manufacturing Process

According to another aspect of the present invention, there is provided a process of preparing the particle, comprising the steps of:

providing an amphiphilic copolymer comprising a first block and a second block, wherein the second block has a solubility greater than the first block;

mixing the copolymer with a first solvent to form a first solution;

mixing an organometallic precursor with a second solvent, thereby forming a complex;

aging the complex, thereby forming a cluster;

mixing the first solution with the cluster thereby forming a mixture;

adding an aqueous solution to the mixture, thereby forming the particle.

In some embodiments, the particle is a hybrid particle comprising the amphiphilic copolymer and the metal oxide, as described hereinabove.

In some embodiments, the process comprises mixing the amphiphilic copolymer with a first solvent to form a first solution. In some embodiments, a first solution comprises the amphiphilic copolymer self-assembled, so as to form of a micellar structure.

In some embodiments, the concentration of the amphiphilic copolymer within the first solution ranges from 0.1 to 50% w/v, from 0.1 to 1% w/v, from 1 to 3% w/v, from 3 to 5% w/v, from 5 to 7% w/v, from 7 to 10% w/v, from 10 to 15% w/v, from 15 to 20% w/v, from 20 to 30% w/v, from 30 to 40% w/v, from 40 to 50% w/v, including any range or value therebetween.

In some embodiments, the first solvent is an organic solvent comprising less than less than 5% w/w, less than 3% w/w, less than 1% w/w, less than 0.1% w/w water. In some embodiments, the first solvent is a water miscible solvent (e.g. a short-chain alcohol, acetone, diacetone alcohol, DMSO, DMF). In some embodiments, the concentration of the amphiphilic copolymer is critical micelle concentration (CMC).

In some embodiments, the process further comprises a step of heating the first solution to a temperature that ranges from about 30° C. to about 50° C. (e.g., 37° C.) prior to the step of adding a cluster solution to the first solution. In some embodiments, the process further comprises incubation at a temperature ranging from 20 to 50° C. In some embodiments, the incubation is for at least one hour. In some embodiments, the incubation results in formation of self-assembled structures. In some embodiments, self-assembled structures are formed prior to the step of adding a cluster solution and/or the step of adding the hydrophobic compound.

In some embodiments, the process further comprises a step of cooling the first solution to a temperature lower than 30° C., thereby stabilizing the amphiphilic copolymer.

In some embodiments, the process comprises providing an organometallic precursor. In some embodiments, the organometallic precursor comprises a metal complex. In some embodiments, the organometallic precursor comprises a transition metal and a plurality of ligands.

Non-limiting examples of ligands include but are not limited to: alkylamines, alkoxides, heteroaromatics, phenols and mercapto, or any combination thereof.

In some embodiments, the ligand is alkoxide. In some embodiments, the organometallic precursor is a transition metal alkoxide.

Non-limiting examples of transition metal alkoxides include but are not limited to: $Ti(OEt)_4$, $Ti(OiPr)_4$, $Ti(OBu)_4$, $Zr(OiPr)_4$, $Zr(OEt)_4$, $Zn(OEt)_2$, and $Zn(OiPr)_4$, or any combination thereof.

In some embodiments, the process comprises mixing the organometallic precursor with a second solvent, thereby forming a complex. In some embodiments, the process comprises mixing the transition metal alkoxide with a second solvent, thereby forming a complex.

In some embodiments, the volume per volume ratio of the organometallic precursor to the second solvent ranges from 1:0.5 to 1:50, from 1:0.5 to 1:1, from 1:1 to 1:2, from 1:2 to 1:3, from 1:3 to 1:4, from 1:4 to 1:5, from 1:5 to 1:7, from 1:7 to 1:10, from 1:10 to 1:20, from 1:20 to 1:30, from 1:30 to 1:40, from 1:40 to 1:50, including any range or value therebetween.

In some embodiments, the second solvent is any organic solvent, which is appropriate for forming a complex. In some embodiments, the second solvent is selected from the group consisting of: an aldehyde and a ketone. In some embodiments, the second solvent has a water content of less than 1% w/w, of less than 0.5% w/w, of less than 0.1% w/w.

Non-limiting examples of solvents suitable for forming a complex include but are not limited to: acetone, methyl ethyl ketone, acetyl acetone, diacetone alcohol, or any combination thereof.

In some embodiments, the process comprises forming a complex. In some embodiments, the complex is metal-oxo-organo complex. In some embodiments, the complex is a transition metal oxo-organo complex. In some embodiments, the complex is a multi-nuclear metal-oxo-organo complex.

In some embodiments, the step of complex formation requires anhydrous conditions, since the organometallic precursor (e.g. Ti-alkoxide) may be extremely moisture sensitive. Exemplary reaction conditions are described in greater detail in the Examples section.

In some embodiments, the complex is represented by Formula 2:

$M_xO_z(OR)_yL_m$, wherein:

M is a transition metal;

each R is independently selected from the group consisting of: an alkyl, a cycloalkyl, an aryl, substituted or unsubstituted;

L is an aldol condensation product;

and x, y, z are from 1 to 30, and m is from 0 to 30.

In some embodiments, the complex is represented by Formula 2a:

$Ti_xO_z(OiPr)_yL_m$.

In some embodiments, the complex is represented by Formula 2b:

$Ti_xO_z(OiPr)_y(O_3C_9H_{15})_m$.

In some embodiments, the complex represented by any of Formulae 2, 2a and 2b is formed spontaneously upon dissolving the organometallic precursor in the second solvent. In some embodiments, the organometallic precursor is a transition metal alkoxide. In some embodiments, the organometallic precursor is titanium alkoxide. In some embodiments, the organometallic precursor is $Ti(OiPr)_4$.

In some embodiments, the complex represented by any of Formulae 2, 2a and 2b is formed spontaneously upon dissolving $Ti(OiPr)_4$ in an anhydrous ketone-based solvent. In some embodiments, the complex represented by any of Formulae 2, 2a and 2b is formed spontaneously upon dissolving $Ti(OiPr)_4$ in acetone.

In some embodiments, upon dissolving $Ti(OiPr)_4$ in acetone a spontaneous ligand exchange reaction occurs. In some embodiments, iso-propoxy ligands are at least partially exchanged with any of: oxo ligands, and/or products of acetone aldol condensation (diacetone alcoholate, mesityl oxide).

The complex formation is characterized by $^1H$-, and $^{13}C$-NMR as described herein below (Examples section). As exemplified by FIGS. 10A-B, and as described in greater detail in Sosnik, et al. (2018) incorporated herein by reference in their entirety, the ligand exchange can be estimated by monitoring the intensity of a signal corresponding to the —$CH_3$ protons (1.2-1.6 ppm) of iso-propoxy groups. A decreasing intensity of the iso-propoxy $CH_3$ signal indicates a dissociation of $Ti(OiPr)_4$ supplemented by the ligand exchange.

Figure 2:
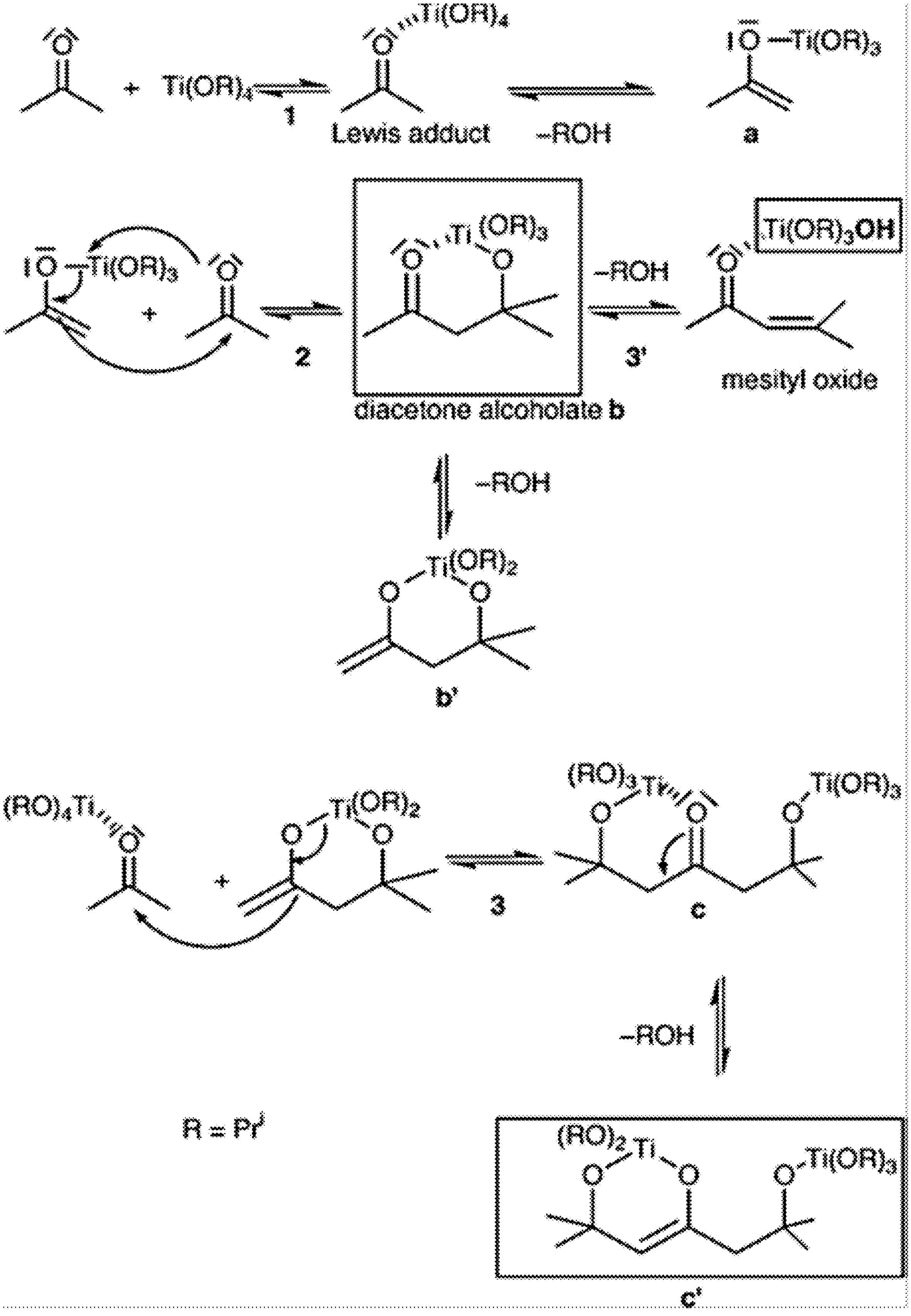
FIG. 2 presents an optional mechanism for the formation of the titanium complex from $Ti(OR)_4$ precursor and acetone.

Without being limited to any particular theory or mechanism, provided herein an optional mechanism for the formation of the complex of Formula 2b from $Ti(OR)_4$ precursor and acetone, as represented by FIG. 2.

Upon mixing the organometallic precursor $Ti(OR)_4$ with acetone, the alkoxy group is exchanged, a donor-acceptor Lewis adduct is formed between Ti(IV) and a carbonyl group of acetone and the adduct converted into a Ti(IV)-enolate complex that favors the stabilization of the enol form of acetone, which is prone to condense with another acetone molecule to form a Ti(IV) diacetone alcoholate (FIG. 2, complex b) that reacts with a third acetone molecule to form a $O_3C_9H_{18}$ tridentate ligand (FIG. 2, complex c).

Figure 10A:
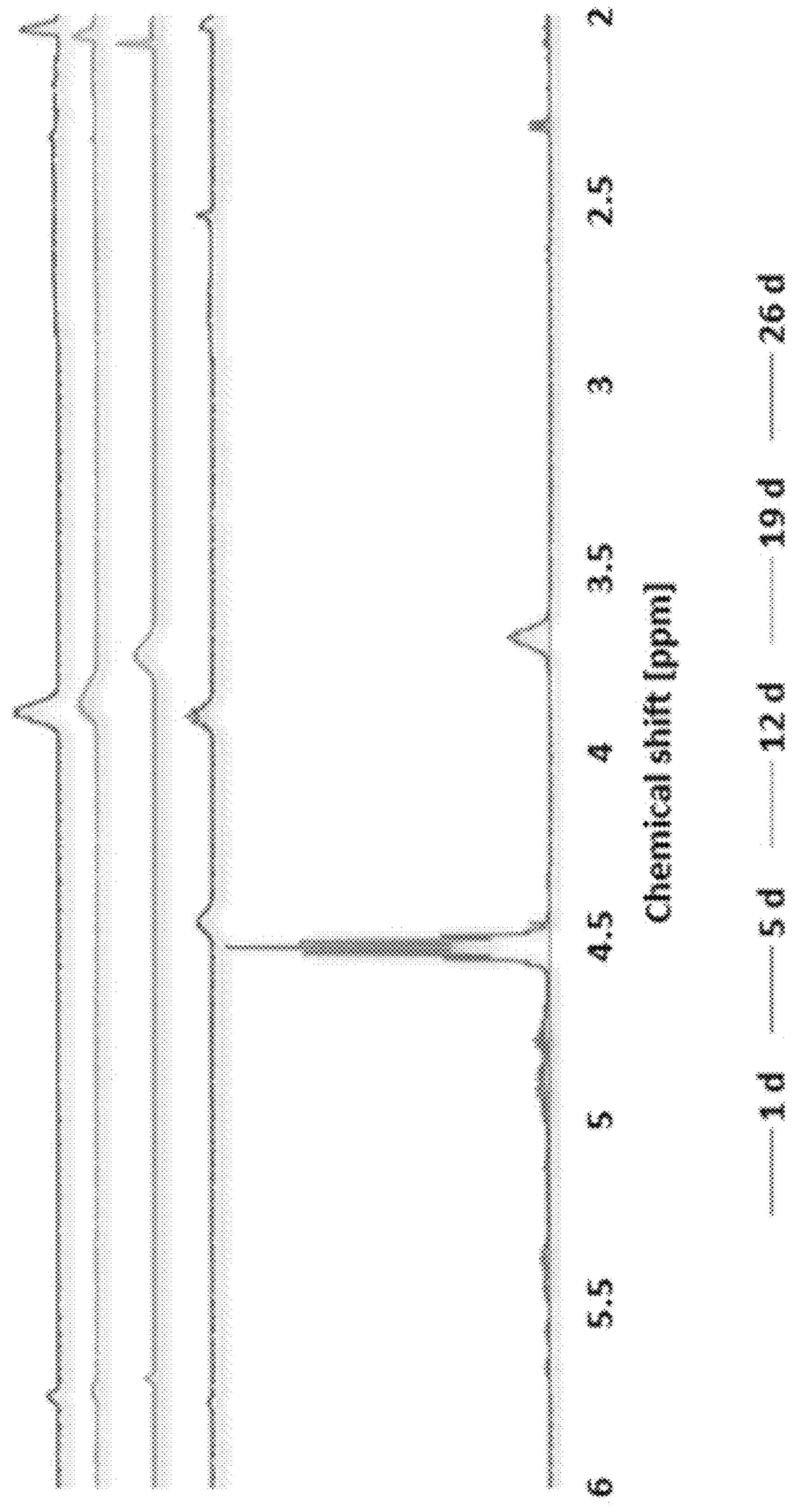
FIGS. 10 A-B present $^1$HNMR graphs, showing Ti(IV) oxo-organo complexes at different aging times.
Figure 10B:
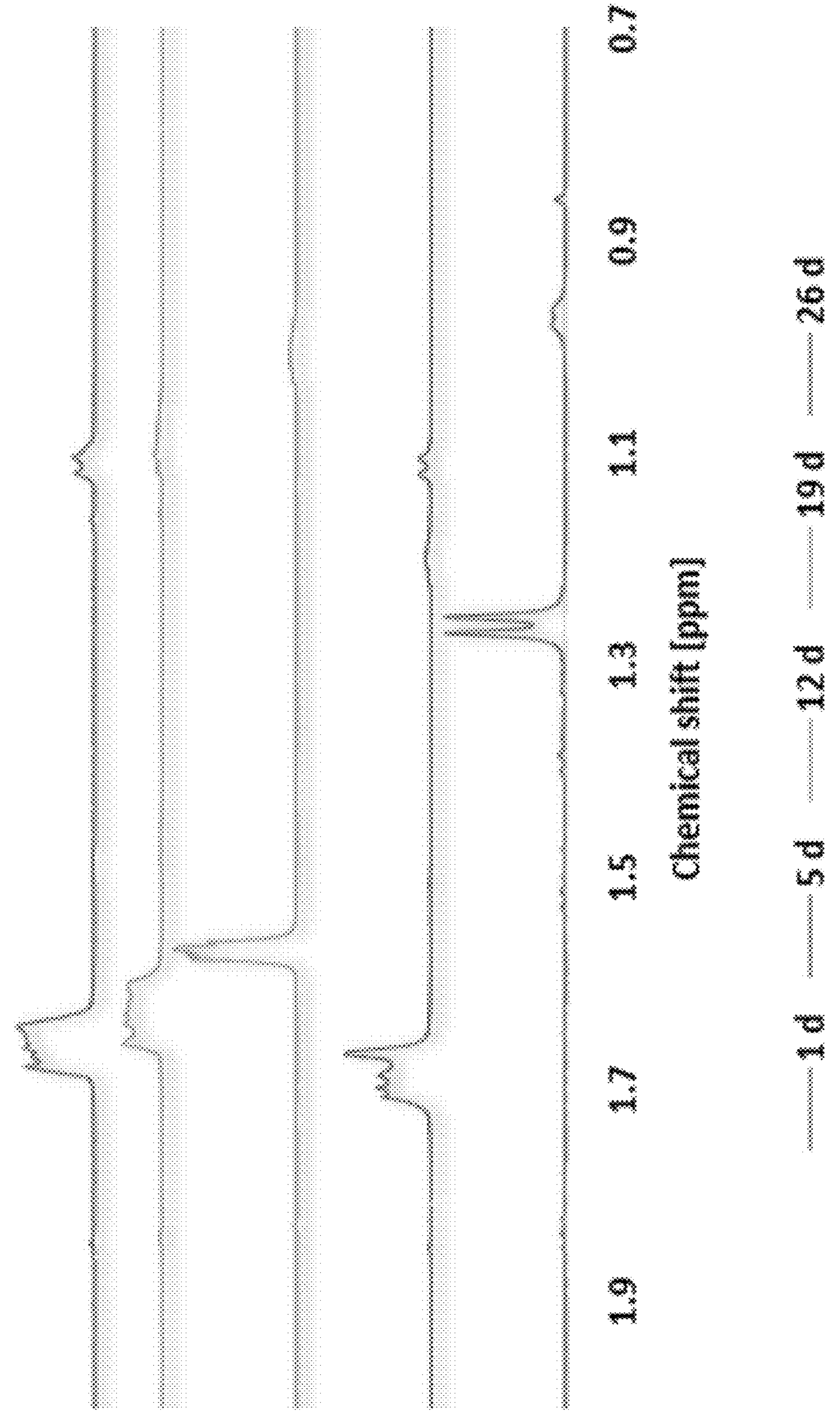

The formation of complexes b and/or c can be monitored by $^1H$-NMR. The absence of characteristic $CH_3$— $^1H$-NMR signal of acetone is explained by its fast aldol reaction with Ti(IV). The doublet in 2.07 and 2.62 ppm is assigned to the geminal hydrogens in —$CH_2$ residues (FIG. 1, complexes b and/or c). In addition, a peak in the 2.10-2.20 ppm range is assigned to the —OH of isopropanol released during condensation (FIGS. 10A-B). The multiplet at 4.49 ppm corresponds to the $(CH_3)_2CH$— proton of the iso-propoxy group of $Ti(OiPr)_4$.

In some embodiments, the complex represented by any of Formulae 2, 2a and 2b is characterized by an enhanced stability to hydrolysis, as compared to the organometallic precursor. The enhanced stability of the multi-nuclear metal-oxo-organo complex to hydrolysis, may be explained by formation of Ti—Ti bonds, stabilizing the resulting complex. The kinetic stability of the complex increases with increasing condensation degree, defined as a ratio between Ti—Ti bonds and Ti—O bonds within the complex. Since the complex has a higher condensation degree than the organometallic precursor In some embodiments, the method comprises aging the complex, thereby forming a cluster. In some embodiments, aging comprises incubating the complex with the second solvent for a time period ranging from 1 to 40 days, from 1 to 10 days, from 10 to 20 days, from 20 to 30 days, from 30 to 40 days, including any range or value therebetween.

In some embodiments, aging is performed at a temperature ranging from 10 to 200° C., from 10 to 50° C., from 10 to 30° C., from 50 to 80° C., from 80 to 100° C., from 100 to 150° C., from 150 to 200° C.

In some embodiments, the particle size is predetermined by aging conditions. In some embodiments, a time period of incubation (also referred to as "aging time") predetermines a particle size. In some embodiments, a temperature of incubation (also referred to as "aging temperature") predetermines a particle size.

In some embodiments, the aging time and/or aging temperature are selected so as to form a particle with a predetermined size. In some embodiments, a particle within an anticipated size range can be formed upon aging the complex for a predetermined time period.

In some embodiments, a predetermined time period is specific for any particle composition. In some embodiments, a predetermined time period varies depending on a chemical composition of the complex. In some embodiments, a predetermined time period varies depending on the transition metal. In some embodiments, a predetermined time period varies depending on the second solvent.

Figure 9:
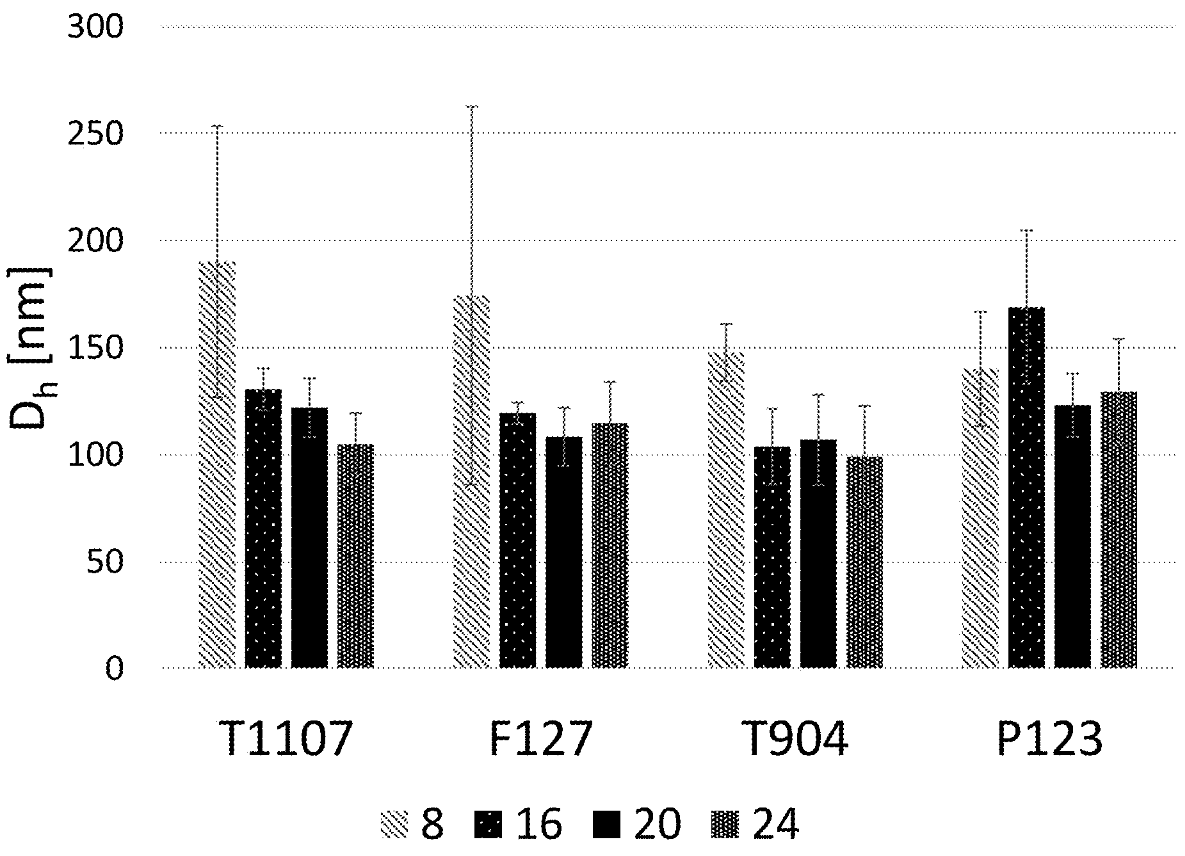
FIG. 9 presents a bar graph showing the particle size of hybrid $TiO_2$/T1107, $TiO_2$/F127, $TiO_2$/P123 and $TiO_2$/T904 nanoparticles at 1:1 volume ratio of the complex to the amphiphilic polymer. Complexes used for the experiment were aged for different time periods (8, 16, 20, and 24 days).

In some embodiments, a predetermined time period depends on any one of: aging conditions, chemical composition of the amphiphilic polymer, and/or a w/w ratio between the metal oxide and the amphiphilic polymer, as exemplified by Table 1 and by FIGS. 7-9.

In some embodiments, the particle size is predetermined by a concentration of any one of the following: the organometallic precursor, the amphiphilic polymer, and the hydrophobic compound.

It will be apparent to those skilled in the art, that the particle size may be further predetermined by a variety of conditions, such as pressure, mixing speed, moisture content of the reagents etc. Additionally, it will be apparent that the exact aging time will depend upon various parameters, such as aging temperature, concentration of the organometallic precursor, etc.

In some embodiments, complex aging results in a cluster formation. In some embodiments, a cluster is characterized by increased condensation degree and increased size, as compared to the complex. The cluster formation is accompanied by dissociation of metal-alkoxide bonds and simultaneous formation of Ti—Ti bonds, resulting in multi-nuclear metal-oxo clusters with an increased condensation degree.

In some embodiments, the cluster is represented by Formula 3:

$M_xO_y$, wherein M is a transition metal, as described hereinabove.

Figure 3:
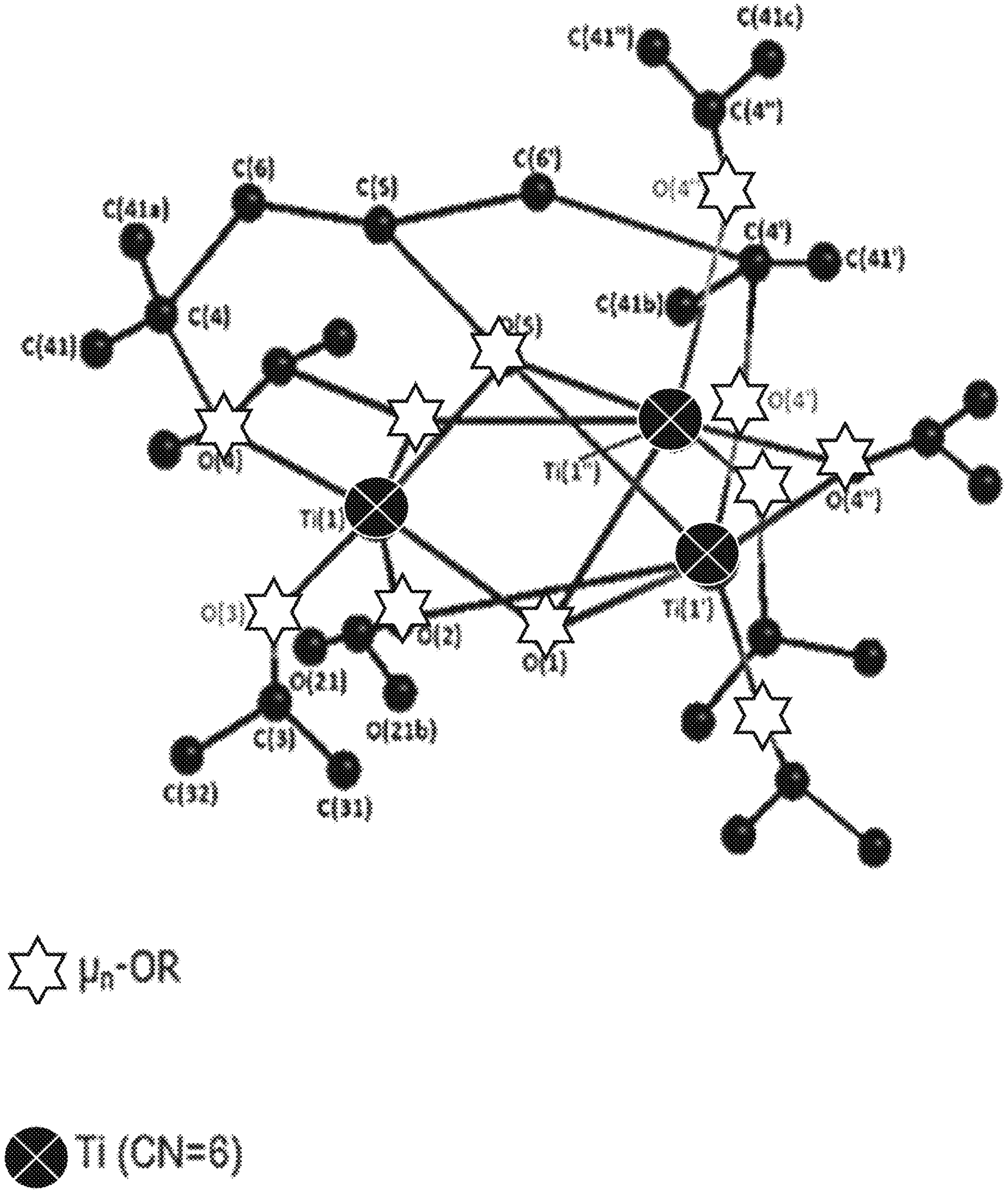
FIG. 3 presents a crystal structure of $Ti_3O(OPri)_7(O_3C_9H_{15})$ cluster formed by Ti(IV) isopropoxide and acetone.

In some embodiments, M is Ti. An exemplary crystal structure of the cluster is represented by FIG. 3. In some embodiments, the cluster formed after a longer aging time is characterized by an increased condensation degree, as compared to the cluster formed after a shorter aging time. In some embodiments, the cluster formed after a longer aging time is characterized by a reduced number of M-alkoxide bonds. In some embodiments, the cluster formed after a longer aging time comprises M-alkoxide bonds mostly on the outer surface of the cluster. In some embodiments, the cluster formed after a longer aging time is characterized by increased nuclearity.

The cluster formation may be characterized by $^{13}$C-NMR and $^{1}$H-NMR, as shown by FIG. 10 and as described in greater detail in Sosnik, et al. (2018) incorporated herein by reference in their entirety. A 1-day complex shows peaks at 25.5-26 and 27.1 ppm that can be assigned to isopropoxy groups of $Ti(OiPr)_4$, free isopropanol and methine carbons in the complex. Some peaks undergo shifting or disappear at later aging times owing to the condensation process that takes place and the release of isopropanol, as observed in 1H-NMR. In addition, the peak of O—$CH(CH_3)_2$ observed at 76.8 ppm at day 1 decreases at day 5 and disappears later on, indicating an increase in the condensation degree and in the size of the Ti(IV)xOy cluster.

In some embodiments, the process comprises mixing the first solution comprising the amphiphilic polymer with the cluster solution thereby forming a mixture, and adding an aqueous solution to the mixture, thereby forming the particle. In some embodiments, the mixture is referred to as "organic mixture".

In some embodiments, the process comprises mixing the first solution comprising the amphiphilic polymer and the hydrophobic compound with the cluster solution thereby forming an organic mixture, and adding an aqueous solution to the organic mixture, thereby forming the particle encapsulating the hydrophobic compound.

In some embodiments, the process comprises adding the organic mixture to an aqueous solution, thereby forming the particle. In some embodiments, the organic mixture is added to an aqueous solution at a ratio ranging from 0.1 to 100 ml/min, from 0.1 to 1 ml/min, from 1 to 5 ml/min, from 5 to 10 ml/min, from 10 to 20 ml/min, from 20 to 50 ml/min, from 50 to 100 ml/min, including any range or value therebetween.

In some embodiments, the v/v ratio of the organic mixture to the aqueous solution ranges from 1:1 to 1:200, from 1:1 to 1:10, from 1:10 to 1:20, from 1:20 to 1:40, from 1:40 to 1:60, from 1:60 to 1:70, from 1:70 to 1:80, from 1:80 to 1:90, from 1:90 to 1:100, from 1:100 to 1:120, from 1:120 to 1:150, from 1:150 to 1:170, from 1:170 to 1:200, including any range or value therebetween.

In some embodiments, the particle is precipitated upon adding the organic mixture to the aqueous solution.

In some embodiments, a w/w ratio of the first solution to the cluster is in a range from 0.1:1 to 1:1, from 1:1 to 1:2, from 1:2 to 1:5, from 1:5 to 1:10, including any range or value therebetween.

In some embodiments, adding an aqueous solution to the mixture results in a hydrolysis of the cluster. In some embodiments, the cluster undergoes a controlled hydrolysis. In some embodiments, adding an aqueous solution to the mixture comprising the cluster results in formation of oxo-polymers, as described herein above. In some embodiments, the cluster undergoes a hydrolysis, thereby forming an amorphous network of oxo-polymers.

In some embodiments, adding an aqueous solution to the mixture results in formation of the hybrid particle, comprising the metal oxide and the amphiphilic polymer, as described herein above.

Without being limited to any particular theory or mechanism, the particle size is predetermined by the condensation degree of Ti(IV)xOy clusters into denser and larger oxo-organo clusters during aging. Formation of, clusters with an increased size leads to the gradual decrease of the relative surface area, thus decreasing the relative concentration of reactive alkoxide moieties exposed at the surface of the complex, making these clusters more kinetically stable to hydrolysis. The enhanced hydrolytic stability of the clusters leads to a slower and more predictable hydrolysis rate, thereby preventing uncontrolled hydrolysis of the metal-oxo clusters. A predictable rate of hydrolysis makes it possible to obtain particles with controllable particle size and size distribution.

Once a sample is nanoprecipitated in water, nanometric oxo-organo complexes collide, coalesce and condense. This condensation relies on the primary hydrolysis of isopropoxy moieties exposed at the nanoparticle surface. Thus, less aged and smaller oxo-organo complexes that display a higher relative surface area and concentration of isopropoxy groups on the surface undergo a more massive hydrolysis and condensation and consequently form larger nanoparticles than more aged and larger counterpart complexes that, owing to a larger size, smaller surface area and a lower relative concentration of isopropoxy groups on the surface, cannot condense substantially and thus, form smaller nanoparticles.

In some embodiments, the step of mixing the amphiphilic copolymer with the first solvent to form the first solution further comprises adding a hydrophobic compound, thereby obtaining the hydrophobic compound encapsulated within the particle. Herein, the hydrophobic compound is as described hereinabove.

An exemplary method of encapsulating the hydrophobic compound (e.g, a drug, such as nitazoxanide) within the particle is described in Example 4. Microscopic images of nitazoxanide loaded particles are presented by FIGS. 14 A-B. Additional microscopic images of nitazoxanide loaded particles are presented in Sosnik, et al. (2018) incorporated herein by reference in their entirety, In some embodiments, the hydrophobic compound is added in form of a solution. In some embodiments, the hydrophobic compound is dissolved in an organic solvent prior to addition to the first solution. In some embodiments, the hydrophobic compound is dispersed in an organic solvent. In some embodiments, the organic solvent is the first solvent or the second solvent.

In some embodiments, w/w ratio of the hydrophobic compound to the amphiphilic copolymer within the first solution ranges from 1:0.5 to 1:40, from 1:0.5 to 1:1, from 1:1 to 1:5, from 1:5 to 1:10, from 1:10 to 1:20, from 1:20 to 1:30, from 1:30 to 1:40, including any range or value therebetween.

In some embodiments, the method further comprises lyophilization to obtain a dry particle. In some embodiments, the method further comprises freeze drying. In some embodiments, the method further comprises spray drying.

The formation of the particle with a desired particle size, may be verified by techniques known in the art. Examples of such techniques include, zeta-potential (Z-potential) measurements, DLS, electron microscopy, etc (see Examples).

Pharmaceutical Compositions

According to another aspect of the present invention, there is provided a pharmaceutical composition, comprising a hybrid particle comprising a transition metal oxide bound to the amphiphilic copolymer, and a hydrophobic compound being encapsulated in the particle e.g., within the core.

In some embodiments, the hydrophobic block of the amphiphilic copolymer forms the core of the hybrid particle. In some embodiments, the hydrophobic block encapsulates the core. In some embodiments, the core comprises a hydrophobic compound. In some embodiments, the core comprises a solution of the hydrophobic compound. In some embodiments, the core comprises a dispersion of the hydrophobic compound. In some embodiments, the hydrophobic block bounds the hydrophobic compound. In some embodiments, the hydrophobic compound interacts non-covalently with the hydrophobic block. In some embodiments, the hydrophobic block encapsulates the hydrophobic compound.

Figure 6:
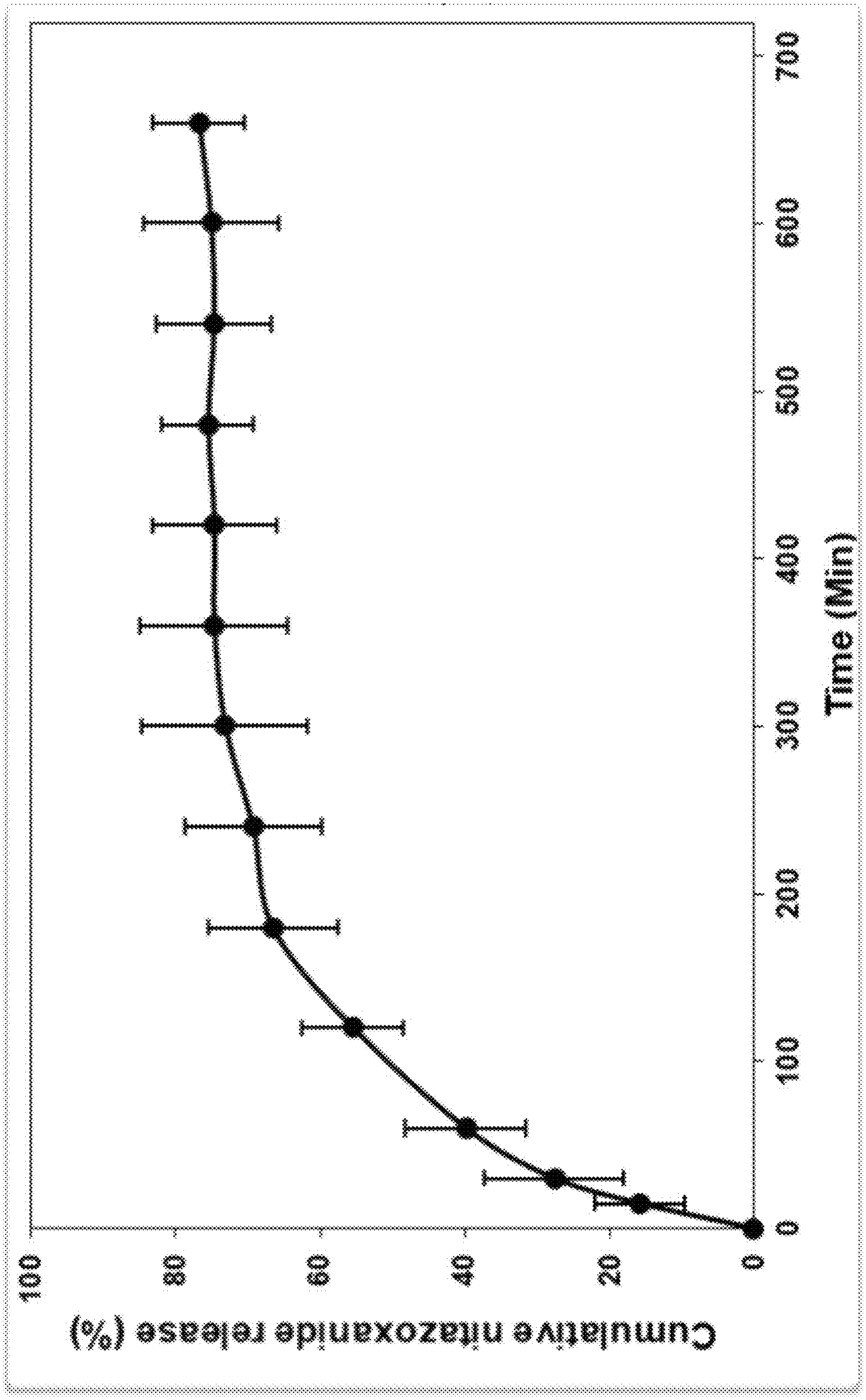
FIG. 6 presents a graph showing cumulative release of nitazoxanide from drug-loaded hybrid TiO2/T1107 nanoparticles produced with a 20-day complex, containing approximately 13% w/w cargo over 12 h.

In some embodiments, the hydrophobic compound bound to the core of the hybrid particle is protected from degradation (e.g. intracellular or extracellular). In some embodiments, the hydrophobic compound bound to the core has an enhanced stability in-vivo. In some embodiments, the hybrid particle is used for targeted delivery of the hydrophobic compound. In some embodiments, the hybrid particle is used for controlled release of the hydrophobic compound (as represented by FIG. 6).

In some embodiments, the pharmaceutical composition further comprises a pharmaceutically acceptable carrier.

As used herein the terms "pharmaceutical composition" or "pharmaceutical product", which are used herein throughout interchangeably, refers to a preparation of one or more of the compositions described herein, or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents (e.g., ibuprofen), anti-viral agents (e.g., efavirenz, darunavir), chemotherapeutic agents (e.g., dasatinib, imatinib, pazopanib, erlotinib, tofacitinib, paclitaxel, camptothecins), anti-bacterial agents (e.g., rifampicin, bedaquiline), anti-histamines (e.g., cinnarizine) and the like. In some embodiments, the purpose of a pharmaceutical composition is to facilitate administration of a hydrophobic compound to a subject.

The terms "pharmaceutical composition" or "pharmaceutical product" are also to be construed to encompass a cosmetic or cosmeceutical product and a nutrient or a nutraceutical product.

The terms "physiologically acceptable carrier" and "pharmaceutically acceptable carrier", which may be interchangeably used, refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, PA, latest edition, which is incorporated herein by reference.

Pharmaceutical products for use in accordance with the present invention thus may be formulated in a conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed, the route of administration utilized and the patient subpopulation (e.g., adult, pediatric, geriatric). The exact formulation, route of administration and dosage can be chosen by the individual physician in view of the patient's condition (see e.g., Fingl et al, 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophthalmically, vaginally, rectally, intranasally). Pharmaceutical composition for intravenous or injectable matrix may comprise an effective amount of a biocompatible, biodegradable controlled release material, the material contained in the polymer is selected from: polyanhydrides, lactic acid and glycolic acid copolymers, polyesters (e.g., polylactic acid, and polyglycolic acid), polyethers, polyorthoesters, polyols, proteins, polysaccharides, and any mixture thereof.

Formulations for topical administration may include but are not limited to lotions, ointments, gels, creams, suppositories, drops, liquids, sprays, powders, films and patches. Conventional pharmaceutical carriers, aqueous, powder or oily bases, thickeners and the like may be necessary or desirable.

Compositions or products for oral administration include powders or granules, suspensions or solutions in water or non-aqueous media, sachets, pills, caplets, capsules, tablets or orally-dissolving films. Thickeners, diluents, flavorings, dispersing aids, emulsifiers or binders may be desirable.

Formulations for parenteral administration may include, but are not limited to, sterile solutions or dispersions which may also contain buffers, diluents and other suitable additives. Slow release compositions are envisaged for treatment.

The amount of a composition to be administered will, of course, be dependent on the subject being treated, in the medical condition being treated for, the severity of the affliction, the manner of administration, the judgment of the prescribing physician, etc.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and anti-histamine.

According to an embodiment of the present invention, the pharmaceutical composition described herein above is packaged in a packaging material and identified in print, in or on the packaging material, for use in the treatment of a disease or disorder, as described herein.

According to another embodiment of the present invention, the pharmaceutical composition is packaged in a packaging material and identified in print, in or on the packaging material, for use in monitoring a disease or disorder, as described herein.

Products of the present invention may, if desired, be presented in a pack or dispenser device, such as an U.S. Food and Drug Administration (FDA) approved kit, or as a diagnostic kit which may contain one or more unit dosage forms containing the disclosed composition. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the FDA for prescription drugs or of an approved product insert.

As used herein throughout, the terms "encapsulate" and/or "entrap" and their grammatical derivatives and conjugations, as used in the context of the present embodiments, relate to any form of accommodating a substance, herein the hydrophobic compound, within a closed e.g., structure, herein the particle. In some embodiments, the entrapment of the hydrophobic compound in the particle, as in the context of the present embodiments, provides complete integration of the hydrophobic compound within the particle, such that the entrapped hydrophobic compounds are fully isolated from the surrounding environment as long as the particle is structurally intact (closed).

As used herein, the terms "encapsulate" and/or "entrap" are meant to encompass cases where the encapsulated entity is solvated, e.g., the encapsulation includes solvent molecules. In cases where the encapsulated entity is surrounded by surface active agents, the encapsulation also includes the surrounding surface-active agents.

The encapsulation, according to the present embodiments, is also meant to include the encapsulation of the solvent in which the encapsulation process takes place and/or the various solutes which are present in the solvent in addition to e.g., the chemical monomers and the hydrophobic compound.

In cases where the hydrophobic compound is not soluble under the conditions of the manufacturing process, the hydrophobic compound can be solubilized by means of surface active molecules that surround the molecules of the hydrophobic compound, which are encapsulated therewith in the encapsulation process.

As described herein above, the void within a core-shell particle wherein the hydrophobic compound is encapsulated is set by the size of the core, the type of the monomers comprising the hydrophobic block, and associating mode there between. Hence, the size of the void within the core-shell particle may be controlled by selecting suitable monomeric units having particular associating groups.

The type of active agent which is suitable for encapsulation within the structure according to the present embodiments depends on several characteristics thereof, such as its size, its solubility in the media in which the self-assembled core-corona structure is formed as well as other chemical compatibility criteria.

In some embodiments, the terms "hydrophobic compound" and "active agent" are used herein interchangeably.

In some embodiments, the phrase "active agent", is referred to a "drug", that is a compound which exhibits a beneficial pharmacological effect when administered to a subject and hence can be used in the treatment of a condition that benefits from this pharmacological effect.

That is, in some embodiments, the biologically or therapeutically active agent is selected from the group consisting of: prophylactic drugs, anticancer drugs, anti-viral drugs, anti-bacterial drugs, anti-fungal drugs, anti-parasite drugs, or combination of drugs, vitamins or metabolites thereof (e.g., retinoic acid), monoclonal antibody, siRNA, RNA, microRNA, DNA, genes, a vaccine, a plasmid, a labeling agent, a diagnostic agent, proteins e.g., enzymes, antigens, a bisphosphonate, an antibacterial, an anti-viral or an antifungal reagent.

For example, a composition which comprises a therapeutically active agent (e.g., a drug) attached to or encapsulated in the particle as described herein, can be efficiently utilized for treating a medical condition that is treatable by the active agent.

In some embodiments, the composition may further comprise an additional targeting moiety attached to the particle, which enhances the affinity of the particle to the desired bodily site where the therapeutic activity should be exerted (e.g., a specific organ, tissue or cells).

In some embodiments, the affinity of the particle to the desired bodily site is predetermined by the particle size.

In some embodiments, the composition may further comprise a shuttling moiety (e.g., cell penetrating peptide) attached to the particle, which may enhance the permeability of the particle in a specific body barrier or cell membrane.

The term "subject" (alternatively referred to herein as "patient") as used herein refers to an animal, e.g., a mammal, e.g., a human, who has been the object of treatment, observation or experiment.

The phrase "anticancer agent" or "anticancer drug", as used herein, describes a therapeutically active agent that directly or indirectly kills cancer cells or directly or indirectly inhibits, stops or reduces the migration and/or proliferation of cancer cells. Anti-cancer agents include those that result in cell death and those that inhibit cell growth, migration, proliferation and/or differentiation. In some embodiments, the anti-cancer agent is selectively toxic against certain types of cancer cells but does not affect or is less effective against normal cells. In some embodiments, the anti-cancer agent is a cytotoxic agent.

The terms "cancer" and "tumor" are used interchangeably herein to describe a class of diseases in which a group of cells display uncontrolled growth (division beyond the normal limits). The term "cancer" encompasses malignant and benign tumors as well as disease conditions evolving from primary or secondary tumors. The term "malignant tumor" describes a tumor which is not self-limited in its growth, is capable of invading into adjacent tissues, and may be capable of spreading to distant tissues (metastasizing). The term "benign tumor" describes a tumor which is non-malignant (i.e. does not grow in an unlimited, aggressive manner, does not invade surrounding tissues, and does not metastasize). The term "primary tumor" describes a tumor that is at the original site where it first arose. The term "secondary tumor" describes a tumor that has spread from its original (primary) site of growth to another site, close to or distant from the primary site.

Non-limiting examples of therapeutically active agents that may be beneficially used in embodiments of the present invention include, without limitation, one or more of an agonist agent, an amino acid agent, an analgesic agent, an antagonist agent, an antibiotic agent, an antibody agent, an antidepressant agent, an antigen agent, an antihistamine agent, an antihypertensive agent, an anti-inflammatory drug, an anti-metabolic agent, an antimicrobial agent, an antioxidant agent, an anti-proliferative drug, an antisense agent, a chemotherapeutic drug, an antiviral, an antiretroviral, a co-factor, a cytokine, a drug, an enzyme, a growth factor, a heparin, a hormone, an immunoglobulin, an inhibitor, a ligand, a nucleic acid, an oligonucleotide, a peptide, a phospholipid, a prostaglandin, a protein, a toxin, a vitamin and any combination thereof.

In some embodiments, the pharmaceutical composition can be used as an ultrasound probe.

In some embodiments, the pharmaceutical composition further comprises an imaging agent.

As used herein, the term "imaging agent" or "labeling agent" refers to a detectable moiety or a probe and includes, for example, chromophores, fluorescent compounds (e.g. NIR dyes), phosphorescent compounds, heavy metal cations (e.g. paramagnetic elements such as Gd3+ based MRI probes), and radioactive labeling compounds (e.g. Ga-68, Tc-99, F-18), as well as any other known detectable moieties.

In any of the methods, uses, compositions, or products, described herein, the products described herein may be utilized in combination with additional therapeutically active agents. Such additional agents include, as non-limiting examples, chemotherapeutic agents, anti-angiogenesis agents, hormones, growth factors, antibiotics, anti-microbial agents, anti-depressants, immunostimulants, and any other agent that may enhance the therapeutic effect of the composition and/or the well-being of the treated subject.

Additional non-limiting examples of active agents include: acetylcholinesterase inhibitors, analgesics and nonsteroidal antiinflammatory agents, anthelminthics, antiacne agents, antianginal agents, antiarrhythmic agents, anti-asthma agents, antibacterial agents, anti-benign prostate hypertrophy agents, immunosuppressants, anticoagulants, antidepressants, antidiabetics, antiemetics, antiepileptics, antifungal agents, antigout agents, antihypertensive agents, antiinflammatory agents, antimalarials, antimigraine agents, antimuscarinic agents, antineoplastic agents, antiobesity agents, antiosteoporosis agents, antiparkinsonian agents, antiproliferative agents, antiprotozoal agents, antithyroid agents, antitussive agent, anti-urinary incontinence agents, antiviral agents, antiretroviral agents, anxiolytic agents, appetite suppressants, beta-blockers, cardiac inotropic agents, chemotherapeutic drugs, cognition enhancers, contraceptives, corticosteroids, Cox-2 inhibitors, diuretics, erectile dysfunction improvement agents, expectorants, gastrointestinal agents, histamine receptor antagonists, hypnotics, immunosuppressants, keratolytics, lipid regulating agents, leukotriene inhibitors, macrolides, muscle relaxants, neuroleptics, nutritional agents, opiod analgesics, protease inhibitors, sedatives, sex hormones, stimulants, vasodilators, essential fatty acids, non-essential fatty acids, proteins, peptides, sugars, vitamins, nutraceuticals, natural agents, or mixtures thereof.

Non-limiting examples of hydrophobic compounds include: antiproliferatives such as paclitaxel, sirolimus (rapamycin), everolimus, biolimus A9, zotarolimus, tacrolimus, and pimecrolimus and mixtures thereof; analgesics and anti-inflammatory agents such as aloxiprin, auranofin, azapropazone, benorylate, diflunisal, etodolac, fenbufen, fenoprofen calcium, flurbiprofen, ibuprofen, indomethacin, ketoprofen, meclofenamic acid, mefenamic acid, nabumetone, naproxen, oxyphenbutazone, phenylbutazone, piroxicam, sulindac; anti-arrhythmic agents such as amiodarone, disopyramide, flecainide acetate, quinidine sulphate; antibacterial agents such as benethamine penicillin, cinoxacin, ciprofloxacin, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim, rifampicin, bedaquiline; anti-coagulants such as dicoumarol, dipyridamole, nicoumalone, phenindione; antihypertensive agents such as amlodipine, guanethidine, benidipine, darodipine, dilitazem, diazoxide, felodipine, guanabenz acetate, isradipine, minoxidil, nicardipine, nifedipine, nimodipine, phenoxybenzamine, prazosin, reserpine, terazosin; anti-muscarinic agents: atropine, benzhexol, biperiden, ethopropazine, hyoscyamine, mepenzolate bromide, oxyphencylcimine, tropicamide; anti-neoplastic agents and immunosuppressants such as aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, paclitaxel, procarbazine, tamoxifen citrate, testolactone, topotecan, SN38, topotecan, irinotecan, exatecan, lurtotecan, imatinib, nilotinib, dasatinib, bosutinib, ponatinib, erlotinib, pazopanib, tofacitinib, doxorubicin, and combinations thereof; beta-blockers such as acebutolol, alprenolol, atenolol, labetalol, metoprolol, nadolol, oxprenolol, pindolol, propranolol; cardiac inotropic agents such as amrinone, digitoxin, digoxin, enoximone, lanatoside C, medigoxin; corticosteroids such as beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; lipid regulating agents such as bezafibrate, clofibrate, fenofibrate, gemfibrozil, probucol; nitrates and other anti-anginal agents such as amyl nitrate, glyceryl trinitrate, isosorbide dinitrate, isosorbide mononitrate, pentaerythritol tetranitrate; antiretrovirals such as nevirapine, efavirenz, etravirine, saquinavir, ritonavir, indinavir, lopinavir, darunavir, atazanavir, fosamprenavir, tipranavir, maraviroc, vicriviroc, rilpivirin, and combinations thereof; antiparasitic drugs such as benznidazole, nifurtimox, nitozoxanide, miltefosine and combination thereof. Other hydrophobic active agents include, but are not limited to, active agents for treatment of hypertension (HTN), such as guanethidine.

In some embodiments, the hydrophobic compounds are new chemical entities under in vitro or in vivo preclinical and clinical evaluation.

In some embodiments, the pharmaceutical composition described hereinabove is suitable to be used in the prophylaxis, diagnosis, or therapy in human or veterinary medicine for the release of biologically active cargos such as drugs, enzymes, proteins, genes, or any other agent with prophylactic, diagnostic, or therapeutic properties, or combinations of these properties.

In some embodiments of the invention, the pharmaceutical composition is a topical composition formulated for administration onto the skin (including eyes, scalp, hair and nails) of a subject.

In some embodiments of the invention, the pharmaceutical composition is an injectable composition.

In some embodiments, the hybrid particles are characterized by high physical stability under unfavored conditions (e.g., extreme dilution) and upon interaction with physiological conditions, thereby preserving the active compound in the core.

In some embodiments, the particles are characterized by a rate-controlling capacity of the active compound.

In some embodiments, the particles are in the form of micro- or nanogel.

In some embodiments, the pharmaceutical composition is formulated for oral administration. In some embodiments, the pharmaceutical composition is formulated for ophthalmic administration e.g., as eye drops, cream, etc. In some embodiments, the pharmaceutical composition is formulated for intranasal administration. In some embodiments, the pharmaceutical composition is formulated for inhalation. In some embodiments, the pharmaceutical composition is formulated as a pharmaceutically acceptable injectable matrix.

According to another aspect of embodiments of the present invention, there is provided a use of the composition described herein in the manufacture of a medicament for treating a medical condition treatable by the therapeutically active agent. In some embodiments the medicament is formulated for oral and/or intravenous administration.

As discussed herein above, a large group of drugs, e.g., chemotherapeutic agents are hydrophobic and exhibit poor solubility in aqueous solution, thus rendering their oral administration problematic. For example, many chemotherapeutic agents are typically administered intravenously. This route of administration is a major source of cost, discomfort and stress to patients, and multiple hospitalizations are required in order to complete the relatively long chemotherapeutic regimen. Thus, the enhancement of water solubility of the chemotherapeutic agent, by encapsulation in the herein described hybrid particle is especially beneficial and may be utilized for treating e.g., cancer and cancer metastases.

In some embodiments, the composition described hereinabove provides desirable solubility factor.

In some embodiments, the solubility factor is solubility of active agent in the hybrid particles divided by the intrinsic solubility of the active agent in a particle-free medium (at 37° C.). A solubility factor of above 1 indicates that more than the amount of active agent soluble in the solvent present.

In some embodiments, the solubility factor is at least 100, least 200, least 300 least 400, least 500, least 600, least 700, least 800, least 900, least 1000, least 1200, least 1300, least 1400, or least 1500.

In some of any of the embodiments of the present invention, the therapeutic agent may also comprise a vasodilator to counteract vasospasm, for example an antispasmodic agent such as papaverine. The therapeutic agent may be a vasoactive agent, generally such as calcium antagonists, or alpha and beta-adrenergic agonists or antagonists. In some of any of the embodiments of the present invention, the therapeutic agent may include a biological adhesive such as medical grade cyanoacrylate adhesive or fibrin glue, the latter being used to, for example, adhere an occluding flap of tissue in a coronary artery to the wall, or for a similar purpose.

In some of any of the embodiments of the present invention, the therapeutic agent may be an antibiotic agent that may be released from the core, optionally in conjunction with a controlled release carrier for persistence, to an infected organ or tissue or any other source of localized infection within the body. Similarly, the therapeutic agent may comprise steroids for the purpose of suppressing inflammation or for other reasons in a bodily site. Exemplary anti-infective agents include, for example, chlorhexidine which is added for improved biocompatibility of articles-of-manufacturing comprising the composition according to some of any of the embodiments of the present invention.

In some embodiments, compositions wherein the hybrid particles are beneficial for use in drug delivery. One exemplary use of such a composition wherein specific drug delivery is crucial is a composition for gene therapy. Such a composition can include a hybrid particle as presented herein and a combination of active agents attached to and/or encapsulated in the particle. In order to design an effective tool for local gene therapy, a hybrid particle may have the following components: a nucleic acid construct, an antisense or any other agent useful in gene therapy, for effecting the desired therapeutic effect within a cell, being attached to the hybrid particle or being encapsulated in a hybrid particle, that can be disassembled under physiological conditions (e.g., being biocleavable by cellular components).

The hybrid particles of the invention may be predestined to have an affinity to the desired location and optionally having a capacity for internalization into the cells at the desired location. Such affinity may be governed by manufacturing particles having a predetermined particle size. The biodistribution of nanoparticles in different tissues and organs is intimately associated with their size. To capitalize on the enhanced permeation and retention (EPR) effect in cancer, the particles should display size of up a few hundreds of nanometers, though this size requirement might vary among solid tumors.

Once reaching its designed target, the hybrid particle is internalized into the cells and once inside the cell, the therapeutic agent is released upon interaction with cellular components that e.g., cleave or hydrolyze either the interactions within the disclosed hybrid metal-oxide copolymeric particle. Thus, the therapeutic agent is delivered to its final target and can exert its therapeutic activity.

Apart from having unique, drug delivery attributes, as detailed herein, the hybrid particles may be used for the sonodynamic therapy (SDT). Due to the ability of $TiO_2$ nanoparticles of controlled size and nanostructure to produce different reactive oxygen species (ROS) upon stimulation with low-intensity ultrasound (US), the hybrid particles of the invention may be used as sonosensitizer for SDT of cancer. ROS generation for targeted cancer therapy has been extensively studied with various photosensitizers utilized for photodynamic therapy (PDT). The basic principle of using ROS generating molecules (e.g. photosensitizers) is due to their ability of inducing DNA cleavage, thus causing cell's apoptosis.

Figure 11B:
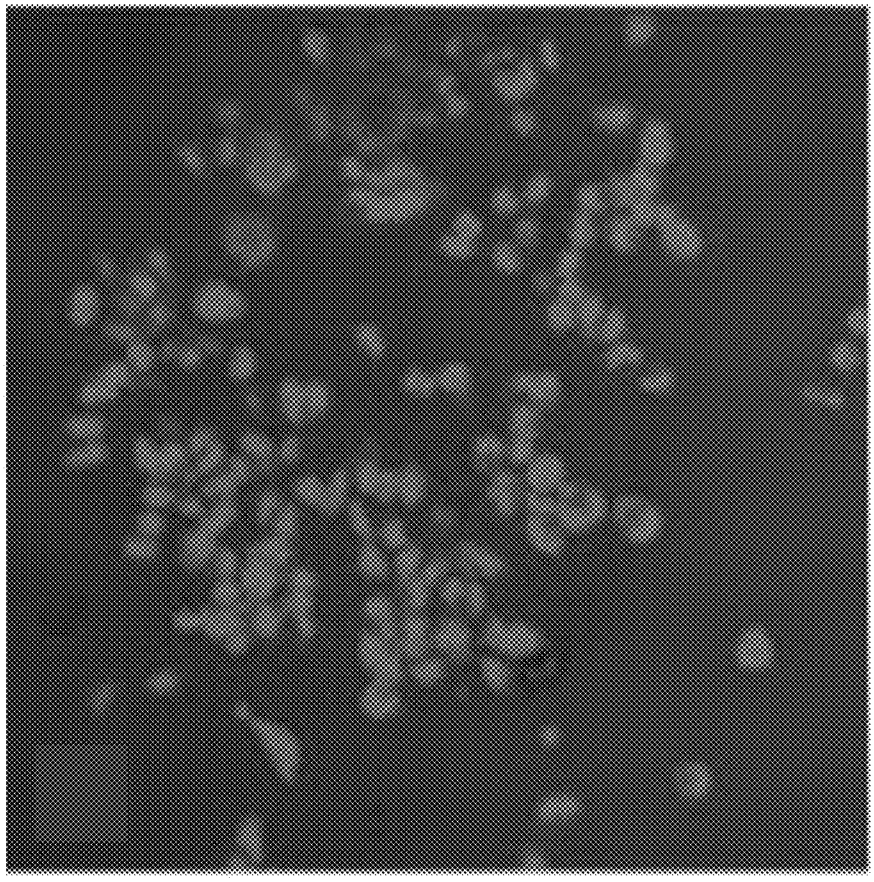
FIGS. 11 A-B present confocal micrographs of rhabdomyosarcoma cells (Rh30) exposed to ultrasound (1 MHz, 10 min) without (FIG. 11A) and with $TiO_2$/T1107 nanoparticles (FIG. 11B) (100 μg/mL), stained with MitoSOX Red.
Figure 11A:
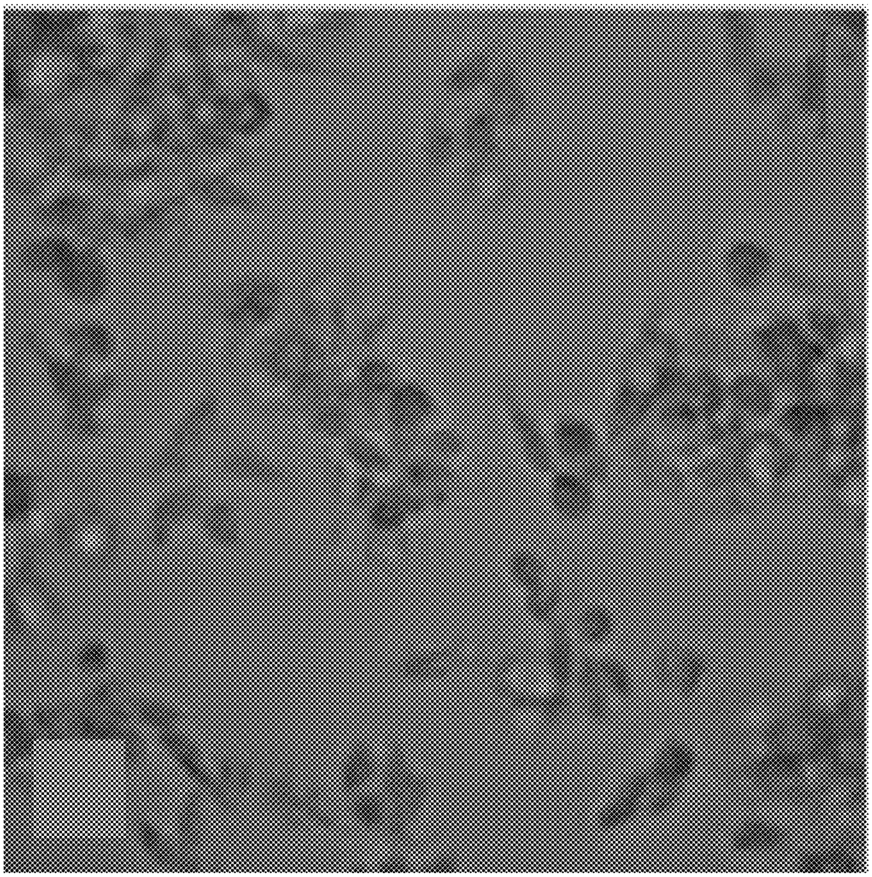

The ability to manufacture hybrid nanoparticles with controlled size and redispersibility can be exploited in SDT, for which excellent size control is required. As represented by FIGS. 11 A-B and by FIG. 12, the hybrid particles of the invention showed a remarkable sono-responsiveness, exhibiting ROS generation in a test-tube and in cell-culture (rhabdomyosarcoma cell line, Rh30). In contrast, counterpart nanoparticles without T1107 presented a much lower ROS production efficiency. These results reveal the fundamental role of the copolymer for ROS production efficiency and the sustained generation of ROS over time which confers flexibility to adjust US excitation regimens. It is important to point out that the US frequency used in this assay is low and frequencies with deeper tissue penetration (1 MHz) are required for preclinical and clinical applications. The evaluation of sonodynamic properties in-vitro is described in Example 6.

In some embodiments, there is provided herein a method for extending the release period in a physiological environment (e.g., blood) of at least one active agent, the method comprising encapsulating at least one active agent in the particle disclosed herein. In some embodiments, active agent is slowly released. In some embodiments, active agent is released in a controlled manner. In some embodiments, active agent is identified as being unstable in the physiological environment.

In some embodiments, the disclosed particle is enabled to encapsulate therein active substance via a variety of interactions depending on the intended use of the desired release characteristics of the active substance, the desired surface properties of the object and many more.

In some embodiments, the particle disclosed herein is designed as uniform and adherent coating and may further be designed to controllably release active substances that are encapsulated therein.

Method of Treatments

According to some embodiments, there is provided a method of monitoring medical conditions such as, but are not limited to, cancer and infections (e.g., viral infection, parasitic infection, fungal infection or bacterial infection).

It is to note that herein, by targeting a therapeutically active agent via the methodologies described herein, the toxicity of the therapeutically active agent is substantially reduced both systemically and locally in body sites where the active agent is not expected to exert its activity. Consequently, besides the use of the particle described herein in a clinically evident disease, optionally in combination with other drugs, these particle may potentially be used as a long term-prophylactic for individuals who are at risk for relapse due to residual dormant cancers.

As further detailed hereinabove, the term "cancer" or "cancer cells" describes a group of cells which display uncontrolled growth (division beyond the normal limits).

As described hereinabove, cancers treatable by the compositions described herein include, but are not limited to, solid, including carcinomas, and non-solid, including hematologic malignancies.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating", or any grammatical derivative thereof, is meant to refer to abrogating, substantially inhibiting, slowing or reversing the progression of a condition, substantially ameliorating clinical or aesthetical symptoms of a condition or substantially preventing the appearance of clinical or aesthetical symptoms of a condition.

It is understood that the composition of the present invention may be administered in conjunction with other drugs, including other antiviral and/or anti-cancer drugs.

As further described hereinabove, the composition of the invention may comprise a labeling agent. Composition comprising a labeling agent may be used in suitable imaging techniques.

Suitable imaging techniques include but are not limited to positron emission tomography (PET), computed tomography (CT), gamma-scintigraphy, magnetic resonance imaging (MRI), functional magnetic resonance imaging (fMRI), magnetoencephalography (MEG), single photon emission computerized tomography (SPECT), computed axial tomography (CAT) scans, ultrasound, fluoroscopy and conventional X-ray imaging, or any combination there between.

The choice of an appropriate imaging technique depends on the nature of the labeling agent, and is within the skill in the art. For example, if the labeling agent comprises Gd ions, then the appropriate imaging technique is MRI; if the labeling agent comprises gamma-emitting radionuclides, an appropriate imaging technique is gamma-scintigraphy; if the labeling agent comprises an ultrasound agent, ultrasound is the appropriate imaging technique; if the labeling agent comprise a near infrared (NIR) dye, NIR is the appropriate technique; etc.

General

As used herein the term "about" refers to ±10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As used herein, the term "alkyl" describes an aliphatic hydrocarbon including straight chain and branched chain groups. The alkyl group has 1 to 100 carbon atoms, and more preferably 1-50 carbon atoms. Whenever a numerical range; e.g., "1-100", is stated herein, it implies that the group, in this case the alkyl group, may contain 1 carbon atom, 2 carbon atoms, 23 carbon atoms, etc., up to and including 100 carbon atoms. In the context of the present invention, a "long alkyl" or "high alkyl" is an alkyl having at least 10, or at least 15 or at least 20 carbon atoms in its main chain (the longest path of continuous covalently attached atoms), and may include, for example, 10-100, or 15-100 or 20-100 or 21-100, or 21-50 carbon atoms. A "short alkyl" or "low alkyl" has 10 or less main-chain carbons. The alkyl can be substituted or unsubstituted, as defined herein.

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" or "cycloalkane" describes an all-carbon monocyclic or fused ring (i.e., rings that share an adjacent pair of carbon atoms) group where one or more of the rings does not have a completely conjugated pi-electron system. The cycloalkyl group may be substituted or unsubstituted, as indicated herein.

The term "aryl" or "aromatic" describes an all-carbon monocyclic or fused-ring polycyclic (i.e., rings which share adjacent pairs of carbon atoms) groups having a completely conjugated pi-electron system. The aryl group may be substituted or unsubstituted, as indicated herein.

The term "alkoxy" describes both an —O-alkyl and an —O-cycloalkyl group, as defined herein.

The term "aryloxy" describes an —O-aryl, as defined herein.

Each of the alkyl, cycloalkyl and aryl groups in the general formulas herein may be substituted by one or more substituents, whereby each substituent group can independently be, for example, halide, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated.

The term "halide", "halogen" or "halo" describes fluorine, chlorine, bromine or iodine.

The term "haloalkyl" describes an alkyl group as defined herein, further substituted by one or more halide(s).

The term "hydroxyl" or "hydroxy" describes a —OH group.

The term "thiohydroxy" or "thiol" describes a —SH group.

The term "thioalkoxy" describes both an —S-alkyl group, and a —S-cycloalkyl group, as defined herein.

The term "thioaryloxy" describes both an —S-aryl and a —S-heteroaryl group, as defined herein.

The term "amine" describes a —NR'R" group, with R' and R" as described herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyrane, morpholino and the like.

The term "carboxy" or "carboxylate" describes a —C(═O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" describes a —C(═O)—R' group, where R' is as defined hereinabove.

The above-terms also encompass thio-derivatives thereof (thiocarboxy and thiocarbonyl).

The term "thiocarbonyl" describes a —C(═S)—R' group, where R' is as defined hereinabove.

A "thiocarboxy" group describes a —C(═S)—OR' group, where R' is as defined herein.

A "sulfinyl" group describes an —S(═O)—R' group, where R' is as defined herein.

A "sulfonyl" or "sulfonate" group describes an —S(═O)$_2$—R' group, where Rx is as defined herein.

A "carbamyl" or "carbamate" group describes an -°C.(═O)—NR'R" group, where R' is as defined herein and R" is as defined for R'.

A "nitro" group refers to a —NO2 group.

A "cyano" or "nitrile" group refers to a —C≡N group.

As used herein, the term "azide" refers to a –N3 group.

The term "sulfonamide" refers to a —S(═O)2-NR'R" group, with R' and R" as defined herein.

The term "phosphonyl" or "phosphonate" describes an —O—P(═O)(OR')2 group, with R' as defined hereinabove.

The term "phosphinyl" describes a —PR'R" group, with R' and R" as defined hereinabove.

The term "alkaryl" describes an alkyl, as defined herein, which substituted by an aryl, as described herein. An exemplary alkaryl is benzyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

As used herein, the terms "halo" and "halide", which are referred to herein interchangeably, describe an atom of a halogen, that is fluorine, chlorine, bromine or iodine, also referred to herein as fluoride, chloride, bromide and iodide.

The term "haloalkyl" describes an alkyl group as defined above, further substituted by one or more halide(s).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples which, together with the above descriptions, illustrate the invention in a non-limiting fashion.

Materials

T1107 (MW=15.0 kg mol-1, HLB of 18-23) was a donation of BASF® (Vandalia, IL) and dialyzed (regenerated cellulose tubular membrane, molecular weight cut off=3500 Da) and freeze-dried before use. Acetone AR (Gadot, Haifa, Israel) was dried with magnesium sulfate anhydrous USP for at least 12 h.

Methods

Preparation of Ti(IV) oxo-organo complexes: to prepare Ti(IV) oxo-organo complexes, titanium tetra-isopropoxide (TTIP, 95% purity, Alfa Aesar®, Ward Hill, MA) was diluted in dry acetone (15 mL) under dry N2 atmosphere and the solution aged at RT for different times and used to produce the nanoparticles.

$^{1}$H- and $^{13}$C-NMR: Oxo-organo complexes (0.5 mL) of different aging time were dissolved in benzene-d6 (1 mL, D, 99.5%, Cambridge Isotope Laboratories, Tewksbury, MA) and $^{1}$H-NMR and $^{13}$C-NMR spectra were recorded in a 400 MHz Bruker Avance III high-resolution spectrometer (Bruker BioSpin GmbH, Rheinstetten, Germany).

ATR-FTIR: Spectra were recorded in an Equinox 55 spectrometer (32 scans with a signal resolution of 4 $cm^{-1}$, Bruker Optics, Inc., Ettlingen, Germany) between 500 and 4000 $cm^{-1}$.

UV-Vis: The UV-Vis spectrum of hybrid nanoparticles produced with 20- and 30-day oxo-organo complexes were dispersed in dimethyl sulfoxide (DMSO, Life Technologies corp., Carlsbad, CA) and measured in a microplate spectrophotometer (ThermoFisher Scientific Oy, Vantaa, Finland). For quantification of the nitazoxanide loading, nanoparticles were dispersed in DMSO and stirred for 48 h (950 rpm) to ensure the complete release of the drug, and the absorbance measured at $\lambda$=439 nm and interpolated in a calibration curve built in DMSO in the 2-12 μg/mL concentration range ($R^2$=0.998). Pristine T1107 was used as blank.

Example 1

Characterization of Oxo-Organo Complexes

The structure and evolution of the oxo-organo complex at different aging times is characterized by $^1$H- and $^{13}$C-NMR (in benzene-d6) and the presence of the characteristic peaks of protons and carbons of the —O—$CH(CH_3)_2$ residues identified and followed up. In general, the aging of the complex and the consequent gradual broadening and, at a later stage, disappearance of some characteristic peaks reveal changes in the degree of condensation and the formation of increasingly larger Ti(IV)xOy core-based clusters (FIGS. 10A-B), and as described in greater detail in Sosnik, et al. (2018) incorporated herein by reference in their entirety.

In $^{13}$C-NMR, a 1-day complex shows peaks at 25.5-26 and 27.1 ppm that can be assigned to isopropoxy groups of TTIP, free isopropanol and methine carbons in the complex. Some peaks undergo shifting or disappear at later aging times owing to the condensation process that takes place and the release of isopropanol, as observed in $^1$H-NMR. In addition, the peak of O—$CH(CH_3)_2$ observed at 76.8 ppm at day 1 decreases at day 5 and disappears later on, indicating again an increase in the degree of condensation and of the size of the Ti(IV)xOy complex, as described in greater detail in Sosnik, et al. (2018) incorporated herein by reference in their entirety.

The complex can be additionally characterized by ATR-FTIR analysis. Spectra show the characteristic bands of Ti(IV) oxo-alkoxides at 2975 $cm^{-1}$ (O—H stretching), 1357 $cm^{-1}$ (—$CH_3$ angular deformation), 1219 $cm^{-1}$ (—$CH_2$ bending), 1126 $cm^{-1}$ (Ti(IV)-O—C stretching), 1003 $cm^{-1}$ (C—O stretching), 849 cm-1 (Ti(IV)-O vibration) and 623 and 528 $cm^{-1}$ (Ti(IV)-O—Ti(IV) stretching). The stretching band of ketone carbonyl at 1711 $cm^{-1}$ confirms the presence of acetone in the medium, though as shown by $^1$H-NMR, mainly in enol form. After 16 days of aging, the spectrum presents fundamental changes such as a decrease in the intensity of the C═O band of acetone and of Ti—O—C and the concomitant increase of the bands of Ti(IV)-O and Ti(IV)-O—Ti(IV) at lower wavenumbers that indicate the progressive condensation of the complex to form larger and more condensed Ti(IV)xOy core-based clusters. The relevant ATR-FTIR spectra are represented in Sosnik, et al. (2018) incorporated herein by reference in their entirety.

Example 2

Synthesis of Hybrid Particles

Oxo-organo complexes of different age (0.5 mL) are homogeneously mixed with 5% w/v T1107 solution in dry acetone (0.5 mL, 1:1 volume ratio) and hand-shaken (3 s). Then, 0.1 mL of the solution was nanoprecipitated in distilled water (4 mL) and hand-shaken (3 s). A similar experiment was conducted with a 20-day old complex without the addition of T1107 and the obtained $TiO_2$ nanoparticles used as control. To prepare drug-loaded hybrid and pure $TiO_2$ nanoparticles, nitazoxanide was dissolved in the T1107 solution in dry acetone (0.5 mL, 1:4 weight ratio to T1107) prior to its mixing with Ti(IV) oxo-organo complex aged 20 days and precipitation in water. Experiments were conducted in triplicate. For the preparation of fluorescently-labeled hybrid nanoparticles, 20% of the weight of T1107 used in the preparation was replaced by T1107 labeled with fluorescein isothiocyanate (FITC, Sigma-Aldrich). Briefly, T1107 (1 g) was dissolved in dry DMF (Bio-Lab Ltd., Jersalem, Israel) to final concentration 20% w/v. FITC (50 mg) dissolved in dry DMF (500 μL), added to the copolymer solution, purged with dry nitrogen (2 min) and the reaction allowed to proceed protected from light (14 h, 32° C.). The resulting solution was dialyzed and freeze-dried. Then, nanoparticles were excited at $\lambda_{ex}$=485 nm and the emission at $\lambda_{em}$=538 nm measured in a Fluoroskan plate reader (Thermo Fisher Scientific Oy). Visualization of the fluorescence was carried out with a ENF-280C/FE lamp (Westbury, NY) at $\lambda$=365 nm.

A glucosylated derivative of T1107 was synthesized by the microwave-assisted ring opening reaction of T1107 with D-(+)-glucono-1,5-lactone (Alfa Aesar, Hayesham, UK) using tin(II) 2-ethylhexanoate ($SnOct_2$, Sigma-Aldrich) as catalyst in a Multiwave Pro Microwave Reaction System with 16HF100 rotor (Anton Paar, Ashland, VA). In a similar way, the use of a glucosylated derivative of T1107 that shows active targeting in pediatric patient-derived solid tumors in vivo and a 20-day aged oxo-organo complex resulted in hybrid nanoparticles with a size of 160 nm.

Other hybrid particles (FIGS. 7-9) comprising amphiphilic copolymers such as F127, P123 and T904 having various w/w ratios of PEG:PPG, were manufactured as described hereinabove.

Example 3

Characterization of Hybrid Particles

DLS: Dh and PDI of drug-free and drug-loaded $TiO_2$ and hybrid $TiO_2$/T1107 nanoparticles produced with complexes of different age were measured in a Zetasizer Nano-ZS (Malvern Instruments, Malvern, UK) equipped with 633 nm laser at 25° C. Values are expressed as mean±S.D. of three independent samples prepared under identical conditions in different experiments. Data for each single specimen were the result of 5-7 runs.

TGA: TGA was carried out in a Q5000IR Thermogravimetric Analyzer (TA Instruments, New Castle, DE) from RT to 500° C. at a heating rate of 10° C./min under dry N2 flow (25 mL/min). In addition, TGA data were used to estimate the drug content (% w/w) in the hybrid nanoparticles and compare these data to UV-Vis spectrophotometry. The calculation of the drug loading in the hybrid nanoparticles (expressed in % w/w) is done assuming that the final weight loss due to drug and hybrid decomposition was identical to those shown by the free drug and the drug-free hybrid nanoparticles. The drug content % D expressed as % w/w was calculated according to Equation 1:

$$\%\ D=(WL_{drug\text{-}loaded\ hybrid}-WL_{drug\text{-}free\ hybrid})/WL_{drug\text{-}free\ hybrid}\times 100,$$

where $WL_{drug\text{-}loaded\ hybrid}$ and $WL_{drug\text{-}free\ hybrid}$ is the total weight loss of the drug-loaded and drug-free hybrid nanoparticles up to 500° C.

DSC: DSC was conducted in a DSC 2 STARe system simultaneous thermal analyzer with STARe Software V13 (Mettler-Toledo, Schwerzenbach, Switzerland) at a heating/cooling rate of 10° C./min under N2 flow (20 mL/min) and In as standard. The thermal treatment of the samples included three steps: (i) heating from 25 to 400° C. (erasing the thermal history), (ii) cooling from 400 to −80° C. and (iii) heating from −80 to 400° C. Thermal transitions were determined in the second and third stage of the analysis.

PXRD: Freeze-dried hybrid nanoparticles were analyzed by PXRD (MiniFlex II desktop X-Ray diffractometer) to determine the amorphous or crystalline nature of both components. Measurements were conducted in a 2θ range of 5-60° using Cu-Ka radiation (λ=0.15406 nm).

HR-SEM: The size and morphology of the different nanoparticles was visualized by HR-SEM (Zeiss Ultra-Plus FEG-SEM, Carl Zeiss NTS GmbH, Oberkochen, Germany) with an 80 mm2 active area Oxford SDD EDS and In-lens secondary electrons detectors with an energy resolution of 127 eV. Samples were prepared by drop casting on silicon wafer (cz polished silicon wafers <100> oriented, highly doped N/Arsenic, SEH Europe Ltd., Livingston, UK) and drying in a pumped desiccator for 24 h. Then the samples were carbon-coated (5 nm). The size of at least 60 nanoparticles was measured using ImageJ software (National Institutes of Health, Bethesda, MD) and results are expressed as Mean±S.D.

TEM: The morphology and nanostructure of the nanoparticles was initially studied in a 200 KeV (or 120 KeV) TEM with a LaB6 electron source and an FEI Supertwin Objective Lens (Tecnai G2 T20 S-Twin, FEI, Eindhoven, Netherlands). Then, selected samples were analyzed in a FEI/Thermo Fisher Titan Cubed Themis G2 300 with high-tension voltage range of 60-300 Kv and high-resolution energy filter (Gatan Quantum ER965) for sub-eV EELS and energy filtered TEM (including ultrafast dual-EELS capabilities). Dual-X detector (Bruker) with an effective Solid Angle of 1.76sr for fast and precise local (atomic) chemical analysis and a high-resolution Bright-Field/Dark-Field/HAADF STEM system was used. All TEM samples were prepared by drop casting and drying in a pumped desiccator for 24 h on holey carbon-coated grids (Holey Carbon Grids onto 200 Mesh Copper, SPI Supplies®, West Chester, PA).

Regardless of the aging time, results show the formation of a transparent nanodispersion containing the hybrid $TiO_2$/T1107 nanoparticles. This aspect stems from the small size of the nanoparticles. Conversely, when the aged complex is nanoprecipitated in water without the incorporation of the copolymer, the dispersion is very turbid and the particles precipitate fast. In addition, the shorter the aging time, the less controlled the formation of the polymer-free nanoparticles and the more turbid the suspension.

Figure 13B:
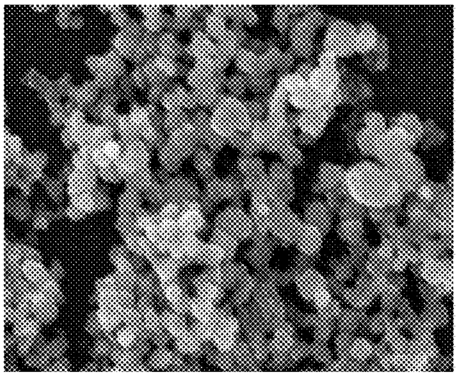

In general, hybrid nanoparticles are almost spherical (FIG. 13A) and display a relatively smooth surface. $TiO_2$ nanoparticles produced without the addition of T1107 show larger sizes and less uniform morphology than hybrid counterparts of identical age and they seem to be partly fused together (FIG. 13B). Remarkably, the longer the aging time, the smaller the size of the $TiO_2$/T1107 nanoparticles (FIG. 13A); e.g., HR-SEM sizes decrease from 230±169 nm at day 1 to 26±6 nm at day 36 (Table 1). S.D. values also decrease for longer aging. DLS data follow the same trend; hydrodynamic diameters (Dh) decrease from 228±30 nm at day 1 to 53±6 nm at day 36 (Table 1). The increase of the hydrodynamic diameter (Dh) measured by DLS with respect to HR-SEM especially for smaller nanoparticles stems from the more substantial effect of PEGylation on the size. In addition, polydispersity index (PDI) values are between 0.200 and 0.540 and tend to decrease for longer aging times (Table 1). Furthermore, DLS analysis reveals the extremely high physical stability of the hybrid nanoparticles in suspension due to the surface modification with hydrophilic PEG blocks that prevents agglomeration by steric stabilization, as opposed to the polymer-free counterparts that are extremely instable and agglomerate and precipitate very fast. Other aspects related to the synthesis and characterization of $TiO_2$/T1107 hybrid nanoparticles (e.g., DLS measurements, TGA, DSC and PSRD graphs), are described in Sosnik, et al. (2018) incorporated herein by reference in their entirety.

Example 4

Synthesis and Characterization of Drug-Loaded $TiO_2$/T1107 Hybrid Nanoparticles To nano-encapsulate nitazoxanide, the synthetic method described in Example 2 is slightly modified and the drug is homogeneously mixed with the complex or the complex/T1107 mixture before the aqueous-phase nanoprecipitation stage to produce drug-loaded $TiO_2$ and hybrid $TiO_2$/T1107 nanoparticles, respectively. A 20-day aged oxo-organo titanium complex was used to produce nitazoxanide-loaded nanoparticles.

Figure 14A:
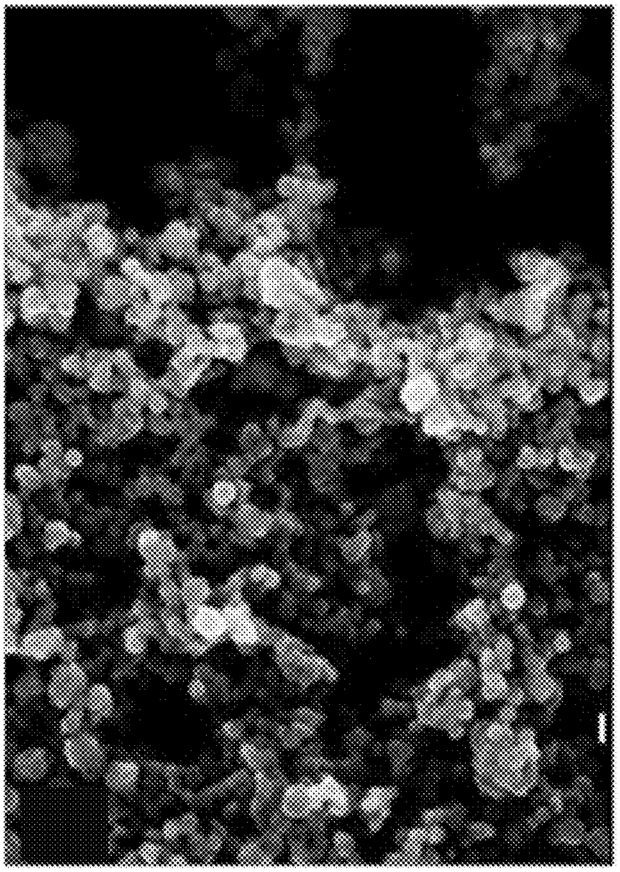
FIGS. 14 A-B present HR-SEM micrographs showing nitazoxanide-loaded $TiO_2$ and hybrid $TiO_2$/T1107 nanoparticles produced by the aqueous-phase nanoprecipitation of a 20-day aged oxo-organo complex.
Figure 14B:
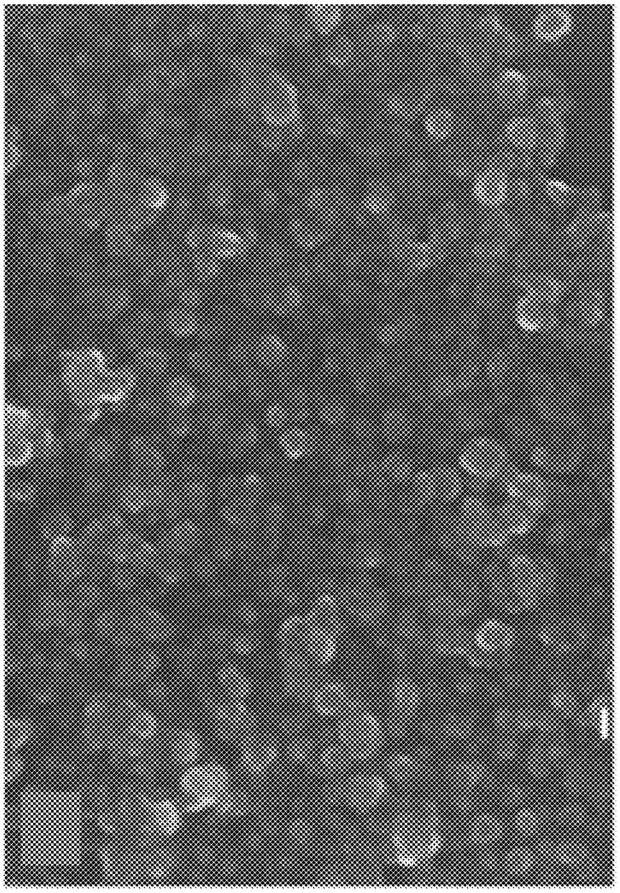

The resulting nanoparticles loaded with nitazoxanide were characterized as described in Example 3. HR-SEM micrographs of nitazoxanide loaded $TiO_2$ nanoparticles and of nitazoxanide loaded hybrid $TiO_2$/T1107 nanoparticles are shown in FIG. 14 A and in FIG. 14 B respectively. Additional micrographs of nitazoxanide loaded $TiO_2$ and hybrid $TiO_2$/T1107 nanoparticles are presented in Sosnik, et al. (2018) incorporated herein by reference in their entirety.

The size and morphology of the drug-loaded nanoparticles characterized by HR-SEM are similar to those shown for drug-free nanoparticles (FIGS. 14 A-B). EDS analysis of S in the bulk of nitazoxanide-loaded $TiO_2$ nanoparticles reveals a relatively low S content of 0.51±0.23 at %, while in the hybrid nanoparticles, the value is 1.09±0.21 at %, representing a 2-fold increase. When the same analysis is conducted on pure drug, a value of 5.06±0.57 at % that is in good agreement with the theoretical value of 4.70 at % is obtained. Complementary DLS analysis of nitazoxanide-loaded $TiO_2$ nanoparticles shows a size of 860±433 nm (85% of % Intensity) with very high PDI of 0.726±0.199 and bad physical stability; a smaller fraction of the material (% Intensity of 15%) cannot be detected by DLS due to Dh>10 um. The results of EDS and DLS analyses are represented in Sosnik, et al. (2018) incorporated herein by reference in their entirety.

Conversely, the size (171±2 nm), the very small size distribution (0.181±0.020) and the almost spherical morphology of drug-loaded hybrid $TiO_2$/T1107 nanoparticles are similar to those of the drug-free counterpart and confirm the key role played by copolymer in the encapsulation and the physical stabilization of the nanoparticles.

The drug payload was accurately quantified by UV-Vis spectrophotometry (λ=439 nm) for which an extraction method is optimized and a calibration curve in dimethyl sulfoxide (DMSO) built. Results indicate a 12.88±1.26% w/w nitazoxanide loading.

Example 5

Drug Release In Vitro

The release of nitazoxanide from hybrid nanoparticles produced with a 20-day complex was assessed utilizing the dialysis membrane method in PBS (0.05M PBS, pH 7.4) prepared with potassium phosphate dibasic ($K_2HPO_4$, Spectrum chemical MFG Corp., Gardena, CA) and monobasic ($KH_2PO_4$, EMD Millipore corp., Billerica, MA). For this, hybrid nanoparticles containing 12.9% w/w according to UV-Vis quantification were diluted to a final nitazoxanide concentration of 1 mg/mL in of pre-heated PBS (37° C.). The dispersion was placed in a dialysis membrane (regenerated cellulose tubular membrane, molecular weight cut off=3500 Da) and immersed in 0.8 L of release medium at 37° C. This volume ratio ensured sink conditions. Aliquots of release medium (30 mL) were removed at predetermined time intervals and replaced by fresh pre-heated (37° C.) PBS to keep the total volume constant. The cumulative drug release was monitored by UV-Vis spectrophotometry at 415 nm using a calibration curve built using serial dilutions in PBS in the 0.01-4 μg/mL concentration range ($R^2$=0.931). Assays were carried out in triplicate and results are expressed as mean±S.D. Average release data was fitted to different models using the DDSolver Software 1.0, a free calculation program used to analyze dissolution or fit drug release data.

The release profile is presented in FIG. 6. Results show a bimodal release profile that is typical of drug-loaded nanoparticles and characterized by the burst release of 40% of the cargo within 1 h and a gradual decrease of the release rate at later time points. This release profile is fitted to different release models utilizing the DDSolver software 1.0. The obtained release data of up to 60% release adjust very well to the Korsmeyer-Peppas model ($R^2$=0.995) described by Equation 2:

$$M_t/M_\infty = k_K \times t^n$$

where $M_t/M_\infty$ is the fraction of released drug, $k_K$ is the Korsmeyer-Peppas release constant and n is the release exponent that indicates the release mechanism.

Considering that the nanoparticles are almost spherical, an n value of 0.548 reveals an anomalous transport that is a combination of diffusion and polymer relaxation/erosion. The complete set of results also adjusts very well to the Peppas-Sahlin model ($R^2$=0.994) described by Equation 3:

$$M_t/M_\infty = k_1 \times t^m + k_2 \times t^{2m}$$

where $M_t/M_\infty$ is the fraction of released drug, $k_1$ and $k_2$ are the Fickian kinetic constant and the polymer erosion/relaxation rate constant, respectively, and the coefficient m is the purely Fickian diffusion exponent which has different values, according to the shape of the delivery system. If the ratio of $k_1/k_2$ is >1, the drug release is mainly governed by diffusion, while if the ratio is <1, mainly by polymer erosion/relaxation.

The hybrid nanoparticles show m of 0.569 that is consistent with anomalous transport (non-Fickian diffusion) and $k_1/k_2$ is >1 that indicates a mainly diffusive release mechanism. This behavior stems from the relatively limited matrix relaxation enabled by the rigid $TiO_2$ scaffold and some extent of swelling of the amphiphilic copolymer within the porous structure of the hybrid nanoparticle.

Example 6

Sonodynamic Properties of the Hybrid Particles

Samples produced according to the protocol described herein above (Example 2), were freeze-dried, redispersed in water at concentration of 1 mg/mL, diluted (0.065-0.5 mg/mL) and the dispersion incubated in an Ultrasonic Bath Elmasonic 5300 (US frequency of 37 kHZ) for 10 min at RT. Then, the ROS probe 2',7'-dichlorofluorescein diacetate was added at a concentration of 20 mg/mL in ethanol (10 μL) to 0.6 mL of nanoparticle dispersion and the fluorescence followed up; this dye does not fluoresce and becomes fluorescent upon oxidation by ROS. The fluorescence was visualized under a UV lamp ($\lambda_{excitation}$=365 nm) and quantified in a fluorescence plate reader ($\lambda_{excitation}$=485 nm, $\lambda_{emission}$=538 nm). The same procedure was carried out in a sample with ROS dye and without nanoparticles that was ultrasonicated (negative control). The negative control did not show any fluorescence, while hybrid amorphous $TiO_2$/T1107 nanoparticles showed very strong fluorescence.

Quantification confirmed the capacity of the hybrid nanoparticles to produce ROS (Table 2). In contrast, counterpart nanoparticles produced without T1107 showed a much lower ROS production efficiency owing to the larger size, limited redispersibility in water and smaller surface area. When these samples were re-analyzed 42 h later (without additional sonication), the intensity of the fluorescence increased 10- to 40-fold for the hybrid nanoparticles and 2- to 10-fold for the polymer-free counterpart. These results indicated the sustained production of ROS over time and revealed the beneficial effect of the copolymer incorporation also in terms of ROS production efficiency and the flexibility to adjust the administration and US excitation regimens to optimize the anti-tumor efficacy.

TABLE 2

Fluorescence induced by sono-excitation of $TiO_2$ and hybrid $TiO_2$/T1107 nanoparticles in vitro using 2',7'-dichlorofluorescein as ROS dye.

| | Emission at 538 nm (a.u) | |
|---|---|---|
| Sample concentration (mg/mL) | T1107-free $TiO_2$ nanoparticles | Hybrid $TiO_2$/T1107 nanoparticles |
| 0.0625 | 0.10 | 0.12 |
| 0.125 | 0.12 | 0.14 |
| 0.25 | 0.11 | 0.18 |
| 0.5 | 0.11 | 0.28 |
| 1 | 0.08 | 0.52 |

Figure 12:
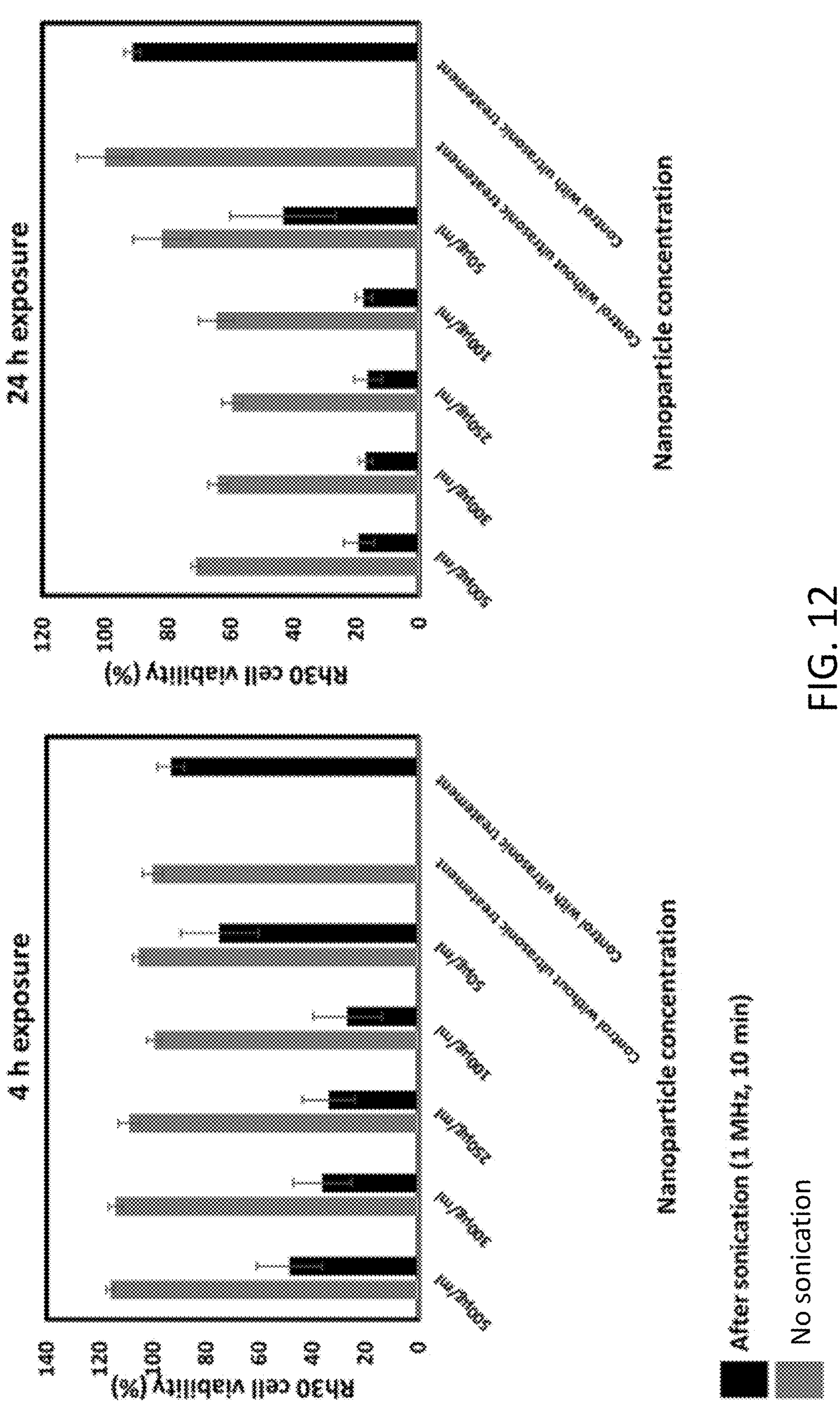
FIG. 12 presents bar graphs showing Rh30 cell viability after 4 h and 24 h incubation with different concentrations of hybrid $TiO_2$/T1107 nanoparticles with and without sonication, as determined by the MTT assay.

Once the sono-responsiveness of the hybrid nanoparticles was confirmed, the cell compatibility and the sonodynamic performance was characterized using therapeutic ultrasound of frequency 1 MHz. For this, a rhabdomyosarcoma cell line (Rh30) was grown in vitro and then, cells were exposed to the hybrid particles. The particles showed very good cell compatibility after 4 h exposure without ultrasound, showing 60-70% viability after 24 h. Once the samples were exposed to ultrasound (1 MHz, 10 min) a sharp decrease was observed (FIG. 12).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition comprising a plurality of particles characterized by an average particle size in a range from 10 to 500 nm as determined by DLS, wherein each of the plurality of particles is a hybrid nanoparticle comprising:

(i) an amphiphilic block-copolymer comprising at least one first block forming a hydrophobic core, and at least one second block having a water solubility greater than said first block; and (ii) a transition metal oxide consisting of titanium oxide in an amorphous state;

wherein said transition metal oxide is bound to said amphiphilic block-copolymer;

wherein the amphiphilic block-copolymer is a sole polymer in the composition; wherein the amphiphilic block-copolymer and the transition metal oxide are homogeneously distributed within the hybrid nanoparticle; wherein said at least one first block is PPG and wherein said at least one second block is PEG; and wherein said amphiphilic block-copolymer is a PEG-PPG block copolymer characterized by an average molecular weight (Mw) of between 500 and 20000 Da.

2. The composition of claim 1, wherein said amphiphilic block-copolymer is characterized by an average molecular weight (Mw) of between 1000 and 10000 Da.

3. The composition of claim 1, wherein said amphiphilic block-copolymer is characterized by spontaneous self-assembly above a critical micellar concentration (CMC) in an aqueous solution; and wherein said amphiphilic block-copolymer is characterized by a hydrophilic-lipophilic balance (HLB) value that ranges from 1 to 24.

4. The composition of claim 1, further comprising a hydrophobic compound; wherein said hydrophobic compound is water-insoluble, and wherein said PEG-PPG block copolymer is selected from

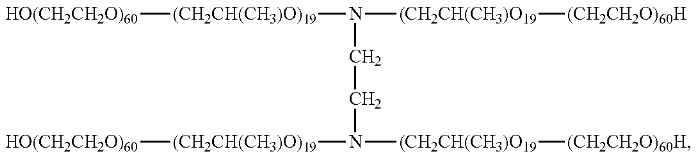

, $HO(CH_2CH_2O)_{101}—(CH_2CH(CH_3)O_{56}—(CH_2CH_2O)_{101}H$, $HO(CH_2CH_2O)_{20}—(CH_2CH(CH_3)O_{70}—(CH_2CH_2O)_{20}H$, and

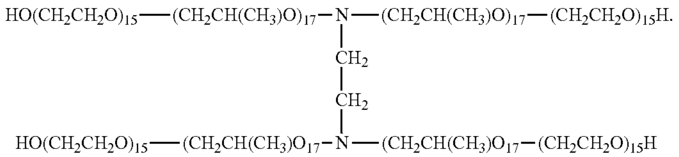

.

5. The composition of claim 4, wherein the hydrophobic compound is selected from the group consisting of: a pharmaceutically active agent, a labeling agent, a diagnostic agent, a prophylactic agent, a nutraceutical, or any combination thereof; and wherein a w/w concentration of said hydrophobic compound within said particle ranges from 1 to 50%.

6. The composition of claim 1, wherein said plurality of particles are characterized by sono-responsiveness.

7. The composition of claim 1, wherein any one of: (i) a weight per weight (w/w) ratio of said at least one first block to said at least one second block within said amphiphilic block-copolymer is in a range from 1 to 99%; (ii) a w/w ratio of said metal oxide to said amphiphilic block-copolymer ranges from 10 to 90% of said nanoparticle; and (iii) said particle retains its structural and chemical identity in a physiological environment for at least 2 h.

8. The composition of claim 1, wherein said plurality of particles is characterized by an average particle size in a range from 10 to 300 nm and a polydispersity index being in a range from 0.01 to 0.3, as determined by DLS.

9. The composition of claim 8, wherein less than 10% of said plurality of particles undergo aggregation in an aqueous dispersion after two weeks of storage at a temperature between 15° C. to 30° C.

10. A composition comprising a plurality of particles characterized by an average particle size in a range from 10 to 500 nm as determined by DLS, wherein each of the plurality of particles is a hybrid nanoparticle comprising an amphiphilic block-copolymer and a transition metal oxide consisting of titanium oxide in an amorphous state; wherein the amphiphilic block-copolymer is a sole polymer in the composition; wherein the amphiphilic block-copolymer and the transition metal oxide are homogeneously distributed within the hybrid nanoparticle; and wherein said amphiphilic block-copolymer is a PEG-PPG block copolymer selected from

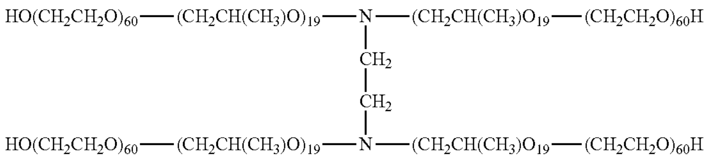

and $HO(CH_2CH_2O)_{101}$—$(CH_2CH(CH_3)O)_{56}$—$(CH_2CH_2O)_{101}H$.

11. A method for treating a medical condition, comprising administering the pharmaceutical composition of claim 1 to a subject in need thereof, thereby treating said medical condition.

12. The method of claim 11, further comprising applying an acoustic wave to said subject, thereby generating reactive oxygen species.

13. A process of manufacturing the particle of claim 1, comprising the steps of:

providing an amphiphilic copolymer comprising a first block and a second block, wherein the second block has a solubility greater than said first block; wherein said first block is PEG and wherein said second block is PPG; and wherein said amphiphilic block-copolymer is a PEG-PPG block copolymer;

mixing said amphiphilic copolymer with a first solvent to form a first solution;

mixing an organometallic precursor with a second solvent, thereby forming a complex;

aging said complex, thereby forming a cluster;

mixing the first solution with the cluster thereby forming a mixture;

adding an aqueous solution to said mixture, thereby forming said particle.

14. The process of claim 13, wherein said aging comprises incubating said complex with said second solvent at a temperature ranging from 10 to 100° C., for a time period ranging from 1 to 40 days, optionally wherein said aging predetermines a size of said particle.

15. The process any one of claim 13, wherein said mixing further comprises adding a hydrophobic compound, thereby obtaining said hydrophobic compound encapsulated within said particle.

16. The process of any one of claim 13, further comprising freeze-drying and/or spray-drying said particle to obtain a dry particle.

17. The process of any one of claim 13, wherein said second solvent has a water content of less than 1% w/w.

18. The process of any one of claim 13, wherein said second solvent is selected from the group comprising an aldehyde and a ketone.

19. The process of claim 13, wherein said organometallic precursor comprises a transition metal alkoxide.

* * * * *